United States Patent
Auricchio et al.

(10) Patent No.: US 11,560,406 B2
(45) Date of Patent: *Jan. 24, 2023

(54) ANTI-ANDROGEN PEPTIDES AND USES THEREOF IN CANCER THERAPY

(71) Applicant: CANCER RESEARCH TECHNOLOGY LIMITED, London (GB)

(72) Inventors: Ferdinando Auricchio, Naples (IT); Antimo Migliaccio, Naples (IT)

(73) Assignee: CANCER RESEARCH TECHNOLOGY LIMITED, London (GB)

(*) Notice: Subject to any disclaimer, the term of this patent is extended or adjusted under 35 U.S.C. 154(b) by 527 days.

This patent is subject to a terminal disclaimer.

(21) Appl. No.: 15/918,268

(22) Filed: Mar. 12, 2018

(65) Prior Publication Data

US 2018/0271933 A1  Sep. 27, 2018

Related U.S. Application Data

(63) Continuation of application No. 14/575,065, filed on Dec. 18, 2014, now Pat. No. 9,919,023, which is a continuation of application No. 12/531,415, filed as application No. PCT/EP2008/053127 on Mar. 14, 2008, now abandoned.

(60) Provisional application No. 60/895,424, filed on Mar. 16, 2007.

(51) Int. Cl.
| | | |
|---|---|---|
| C07K 14/705 | (2006.01) | |
| C07K 7/08 | (2006.01) | |
| C07K 14/72 | (2006.01) | |
| A61K 38/08 | (2019.01) | |
| A61K 38/10 | (2006.01) | |
| C07K 7/06 | (2006.01) | |

(52) U.S. Cl.
CPC ........... *C07K 7/08* (2013.01); *A61K 38/08* (2013.01); *A61K 38/10* (2013.01); *C07K 7/06* (2013.01); *C07K 14/721* (2013.01)

(58) Field of Classification Search
None
See application file for complete search history.

(56) References Cited

U.S. PATENT DOCUMENTS

| | | |
|---|---|---|
| 7,060,463 B2 | 6/2006 | Fowler et al. |
| 7,160,989 B2 | 1/2007 | Logan et al. |
| 9,919,023 B2 * | 3/2018 | Auricchio .............. A61K 38/08 |
| 2004/0071731 A1 | 4/2004 | Fitzgerald |
| 2010/0189776 A1 | 7/2010 | Auricchio |
| 2010/0286229 A1 * | 11/2010 | Gurova .............. G01N 33/5011 514/44 A |

FOREIGN PATENT DOCUMENTS

| | | | |
|---|---|---|---|
| WO | 9846250 A1 | 10/1998 | |
| WO | 0001813 A2 | 1/2000 | |
| WO | WO-0001813 A2 * | 1/2000 | ........... C07K 14/721 |

OTHER PUBLICATIONS

T.M. Allen et al., "Large unilamellar liposomes with low uptake into the reticuloendothelial system", FEBS Lett., 223 (1): 42-46 (1987).
V. Boonyaratanakomkit et al., "Progesterone Receptor Contains a Proline-Rich Motif that Directly Interacts with SH3 Domains and Activates c-Src Family Tyrosine Kinases", Molecular Cell, 8: 269-280 (2001).
M. Capecchi, "High Efficiency Transformation by Direct Microinjection of DNA into Cultured Mammalian Cells", Cell, 22: 479-488 (1980).
L. Carpino et al., "The 9-Fluorenylmethoxycarbonyl Amino-Protecting Group", J. Org. Chem., 37(22) 3404-3409 (1972).
G. Castoria et al., "Non-transcriptional action of oestradiol and progestin triggers DNA synthesis", the EMBO Journal, 18(9): 2500-2510 (1999).
G. Chodak et al., "Nuclear Localization of Androgen Receptor in Heterogeneous Samples of Normal, Hyperplastic and Neoplastic Human Prostate", J. Urol., 147: 798-803 (1992).
D. Clapp, "Somatic Gene Therapy into Hematopoietic Cells", Clinics in Perinatology, 20(1): 155-168 (1993).
P. Couvreur et al., "Nanocapsules: A New Type of Lysosomotropic Carrier", FEBS Lett., 84(2): 323-326 (1977).
P. Couvreur, "Polyalkylcyanoacrylates as Colloidal Drug Carriers", CRC Crit. Rev. Ther. Drug Carrier Sys . . . , 5: 1-20 (1988).
D. Curiel et al., "Adenovirus enhancement of transferrin-polylysine-mediated gene delivery", Proc. Natl. Acad. Sci., USA, 88: 8850-8854 (1991).
N. Dawson et al., "Secondary Hormonal Therapy", Advanced therapy of prostate disease, Resnick MI, Thompson MI, eds, Hamilton, Ontario: BC Decker, pp. 378-384 (2000).
L. Denis et al., "Endocrine Treatment in Prostate Cancer", Seminars in Surgical Oncology, 18: 52-74 (2000).
M. Eglitis et al., "Retroviral Vectors for Introduction of Genes into Mammalian Cells", BioTechniques, 6(7): 608-614 (1988).
M. Eglitis et al., "Retroviral-Mediated Gene Transfer Into Hemopoietic Cells", Avd. Exp. Med. Biol., 241: 19-27 (1988).
G. Fields et al., "Solid phase peptide synthesis utilizing 9-fluorenylmethoxycarbonyl amino acids", Int. J. Peptide Protein Res., 35: 161-214 (1990).
J. Fowler et al., "Considerations for the Use of Testosterone with Systemic Chemotherapy in Prostatic Cancer", Cancer, 49: 1373-1377 (1982).

(Continued)

*Primary Examiner* — Michael D Pak
(74) *Attorney, Agent, or Firm* — Entralta P.C.; James F. Fleming; Peter D. Weinstein

(57) ABSTRACT

The present invention relates to isolated or purified or partially purified peptide derived molecules having the following general formula (S1): X-[(Pro)$_n$-His-Pro-His-Ala-Arg-Ile-Lys]$_m$-Y. The peptides are for medical use, in particular as anti-tumoral agents.

9 Claims, 6 Drawing Sheets

Figure 1:
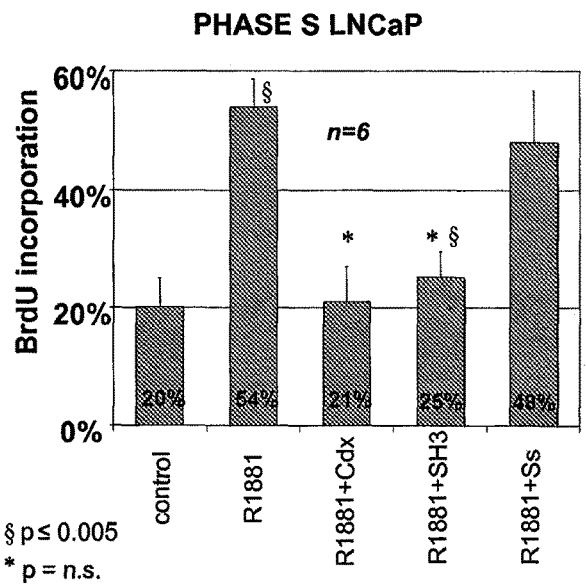
Figure 1:
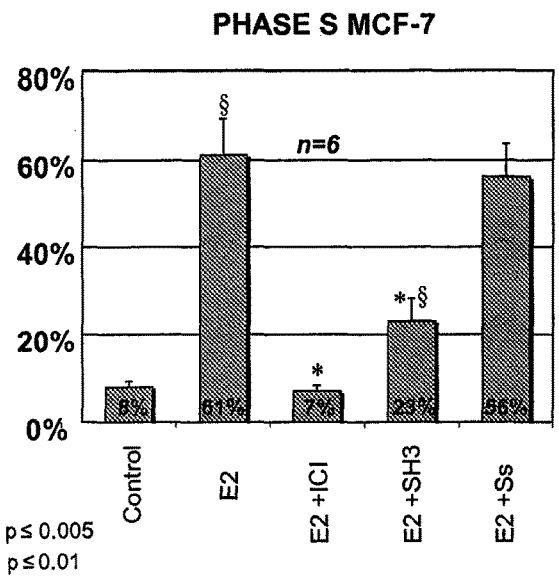
Figure 1:
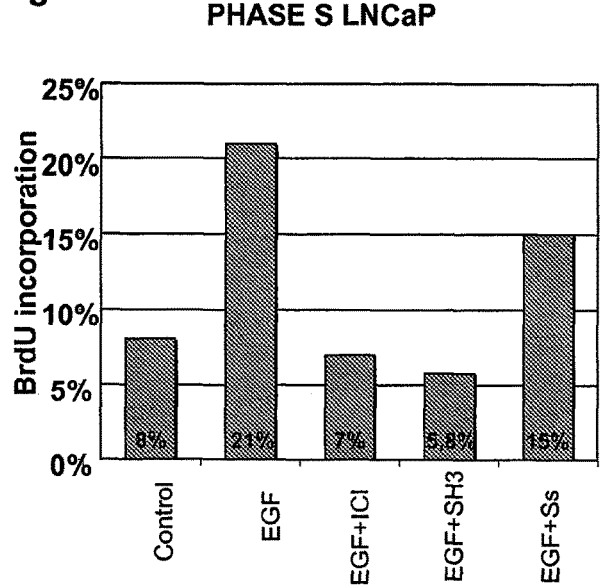
Figure 1:
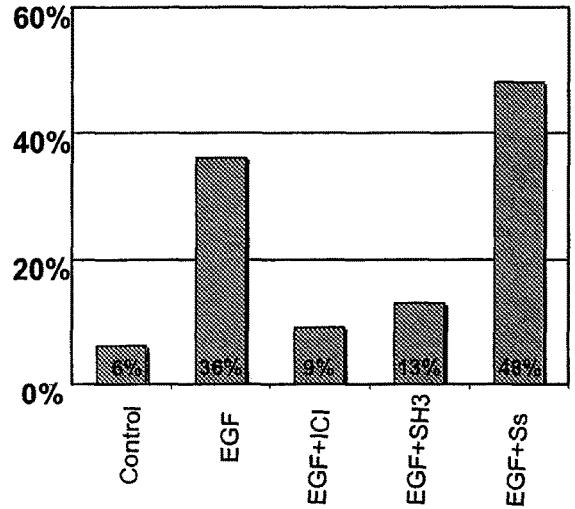

Specification includes a Sequence Listing.

(56) References Cited

OTHER PUBLICATIONS

M. Fromm et al., "Expression of genes transferred into monocot and dicot plant cells by electroporation", Proc. Natl. Acad. Sci. USA, 82: 5824-5828 (1985).
A. Gabizon et al., "Liposome formulations with prolonged circulation time in blood and enhanced uptake by tumors", Proc. Natl. Acad. Sci. USA, 85: 6949-6953 (1988).
F. L. Graham et al., Virology, "Transformation of Rat Cells by DNA of Human Adenovirus 5", 54: 536-539 (1973).
A. Hobisch et al., "Androgen Receptor Status of Lymph Node Metastases From Prostate Cancer", The Prostate, 28: 129-135 (1996).
B. Kay et al., "The importance of being proline: the interaction of proline-rich motifs in signaling proteins with their cognate domains", FASEB J., 14: 231-241 (2000).
D. Lee, "High Androgen Receptor Levels Are Predictive of Decreased Survival in Prostate Cancer", Clin. Prostate Cancer, 2: 13-14 (2003).
A. Migliaccio et al., "Steroid induced androgen receptor-oestradiol receptor B-Src complex triggers prostate cancer cell proliferation", The EMBO Journal, 19(20): 5406-5417 (2000).
A. Migliaccio et al., "Tyrosine kinase/p21ras/MAP-kinase pathway activation by estradiol-receptor complex in MCF-7 cells", The EMBO Journal, 15(6): 1292-1300 (1996).
A. Migliaccio et al., "Steroid Receptor Regulation of Epidermal Growth Factor Signaling through Src in Breast and Prostate Cancer Cells: Steroid Antagonist Action", Cancer Res. 65(22): 10585-10593 (2005).
J. Mohler et al., "Androgen and Glucocorticoid Receptors in the Stroma and Epithelium of Prostatic Hyperplasia and Carcinoma", Clin Cancer Res., 2: 889-895 (1996).
F. Moinfar et al., "Androgen Receptors Frequently Are Expressed in Breast Carcinomas", Cancer, 98(4): 703-711 (2003).
G. P. Moss et al., "Basic Terminology of Stereochemistry", Pure & Appl. Chem., 68(12): 2193-2222 (1996).
H. Rink et al., "Solid-Phase Synthesis of Protected Peptide Fragments Using a Trialkoxy-Diphenyl-Methylester Resin", Tetrahedron Letters, 28(33): 3787-3790 (1987).
A. K. Roy et al., "Regulation of Androgen Action", Vitamins and Hormones, 55: 309-352 (1999).
M. Sadi et al., "Immunohistochemical Study of Androgen Receptors in Metastatic Prostate Cancer", Cancer, 67: 3057-3064(1991).
G. Schatzl et al., "Association of Polymorphisms Within Androgen Receptor, 5 alpha-Reductase, and PSA Genes With Prostate Volume, Clinical Parameters, and Endocrine Status in Elderly Men", The Prostate, 52:130-138 (2002).
Y. Shi et al., "Progestins and antiprogestins in mammary tumour growth and metastasis", Human Reproduction, 9: 162-173-(1994).
P. Siiteri et al., "Testosterone Formation and Metabolism During Male Sexual Differentiation in the Human Embryo", J. Clin. Endocrinol. Metab, 38: 113-125 (1974).
J. Tam et al., "Multiple Antigen Peptide System", Methods in Enzymology, 289: 612-637 (1997).
G. Tuchscherer et al., "Template assisted protein de novo design", Pure & Appl. Chem., 68(11): 2153-2162 (1995).
T. van der Kwast et al., "Androgen Receptors in Endocrine-Therapy-Resistant Human Prostate Cancer", Int. J. Cancer, 48: 189-193 (1991).
G. Verrijdt et al., "Change of Specificity Mutations in Androgen-selective Enhancers", J. Biol. Chem., 275(16): 12298-12305 (2000).
E. Wagner et al., "Transferrin-polycation conjugates as carriers for DNA uptake into cells", Proc. Natl. Acad. Sci. USA, 87: 3410-3414 (1990).
J. C. Williams et al., "Insights into Src kinase functions: structural comparisons", TIBS, 23: 179-184 (1998).
T. Wong et al., "Electric Field Mediated Gene Transfer", Biochemical and Biophysical Research Communications, 107(2): 584-587(1982).
N. Yang et al., "In vivo and in vitro gene transfer to mammalian somatic cells by particle bombardment", Proc. Natl. Acad. Sci. USA, 87: 9568-9572 (1990).
International Search Report from corresponding International Application No. PCT/EP2008/053127.
B. Maillere et al., "Fine Chemical Modifications at N- and C-Termini Enhance Peptide Presentation to T Cells, by Increasing the Lifespan of Both Free and MHC-Complexed Peptides", Molecular Immunology, 32: 1377-1385 (1995).
A. Migliaccio et al., "Inhibition of the SH3 domain-mediated binding of Src to the androgen receptor and its effect on tumor growth", Oncogene, 26: 6619-6629 (2007).
Harlow, "Antibodies a laboratory manual", Cold Spring Harbor Laboratory, pp. 72-77 (1988).

* cited by examiner

LNCaP

| R1881 | − | + | + | + | + |
| Inhib. | − | − | Cdx. | SH3 | Ss |

MCF-7

| $E_2$ | − | + | + | + | + |
| Inhib. | − | − | ICI | SH3 | Ss |

MCF-7

← cyc D1

LNCaP

← cyc D1

| R1881 | - | + | + | + | + |
| Inhib. | - | - | LY | SH3 | Ss |

MCF-7

← cyc D1

LNCaP

← cyc D1

| $E_2$ | - | + | + | + | + |
| Inhib. | - | - | LY | SH3 | Ss |

Fig. 4A
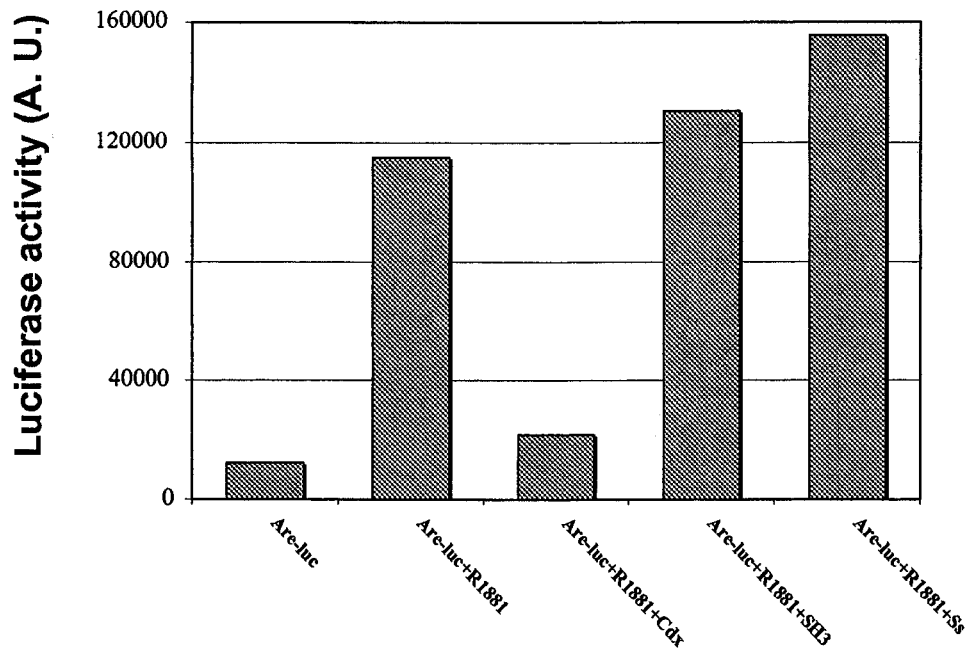
Fig. 4B
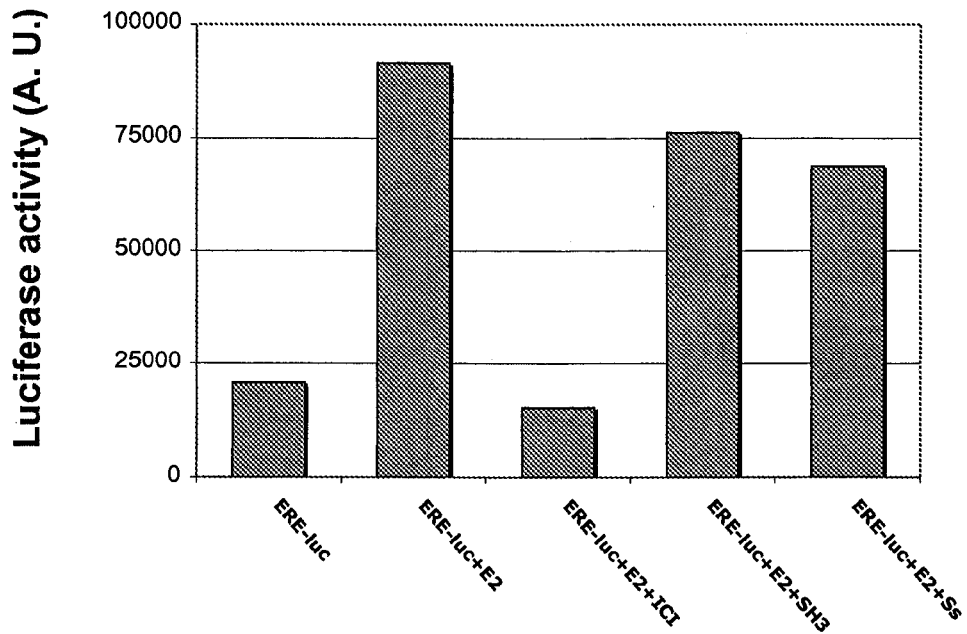
Fig.4

Fig. 6A
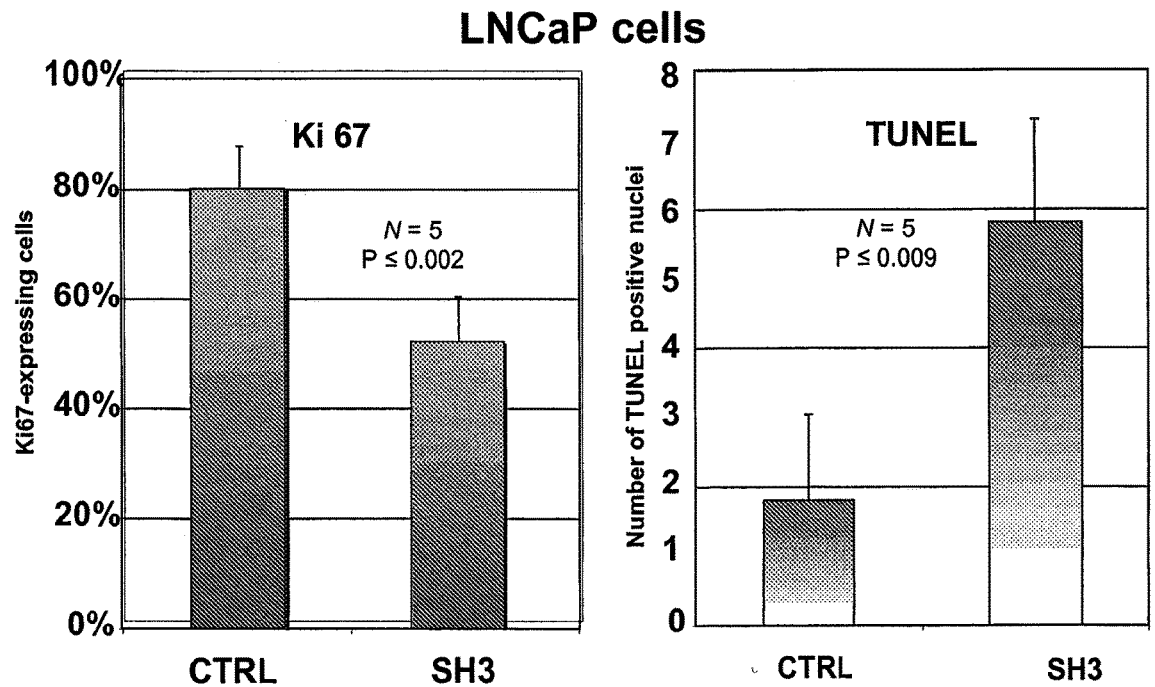
Fig. 6B
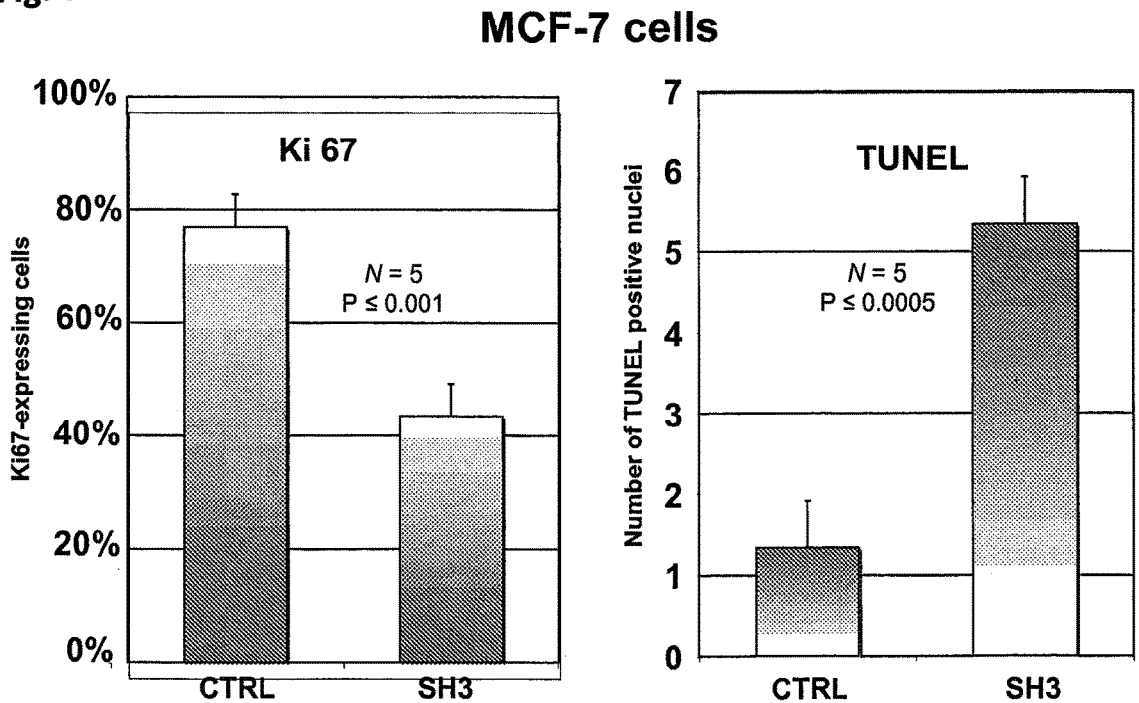
Fig. 6

ANTI-ANDROGEN PEPTIDES AND USES THEREOF IN CANCER THERAPY

CROSS-REFERENCE TO RELATED APPLICATIONS

This application is a continuation of U.S. patent application Ser. No. 14/575,065, filed Dec. 18, 2014, which is a § 371 of International Application No. PCT/EP2008/053127, filed Mar. 14, 2008, which claims the benefit of U.S. Provisional Application No. 60/895,424, filed Mar. 16, 2007. The entire disclosure of each of the aforesaid applications is incorporated by reference in the present application.

BACKGROUND OF THE INVENTION

The present invention relates to native, site specifically mutated, and synthetic peptides comprising portions of the human androgen receptor and composition thereof. The invention also relates to antibodies raised against these peptides and polynucleotides encoding these peptides. Also provided are methods for synthesizing derivatives of these peptides and their use as anti-androgen compositions in the treatment and/or prevention of prostate and/or breast cancers, preparation of pharmaceutical compositions, diagnostic kits, and development of related assays for use in anticancer therapies.

STATE OF THE ART

Androgen Receptor in Human Prostate and Mammary Cancers

The androgen receptor (AR) is a ligand-activated transcriptional regulatory protein that mediates induction of male sexual development and function through its activity with endogenous androgens (Roy et al, 1999). Androgens are generally known as the male sex hormones. The androgenic hormones are steroids, which are produced in the body by the testes and the cortex of the adrenal gland or can be synthesized in laboratory. Androgenic steroids play an important role in many physiologic processes, including the development and maintenance of male sexual characteristics such as muscle and bone mass, prostate growth, spermatogenesis, and the male hair pattern (Siiteri and Wilson, 1974). Endogenous steroidal androgens include testosterone and dihydrotestosterone (DHT). Testosterone is the principal steroid secreted by the testes and is the primary circulating androgen found in the plasma of mates. Testosterone is converted to DHT by the enzyme 5-alpha-reductase in many peripheral tissues. DHT is thus thought to serve as the intracellular mediator for most androgen actions.

Other steroidal androgens include esters of testosterone, such as the cypionate, propionate, phenyl-propionate, cyclopentyl-propionate, isocarporate, enanthate, and decanoate esters, and other synthetic androgens such as 7-Methyl-Nortestosterone.

The two major cancer types that express the androgen receptor (AR) are prostate cancer and breast cancer. Other cancers may also be AR positive. The most common AR positive cancer is prostate cancer. Approximately 80-90% of prostate cancers are dependent on androgen at initial diagnosis, and endocrine therapy of prostate cancer is directed toward the reduction of serum androgens and inhibition of AR (Denis and Griffiths, 2000). However, when androgen ablation therapy ultimately fails, prostate cancer progresses to a hormone refractory state. AR is expressed throughout prostate cancer progression and persists in the majority of patients with hormone refractory disease (Mohler et al., 1996; van der Kwast et al., 1991; Sadi et al. 1991; Chodak et al. 1992; Hobisch et al., 1996). Also, most identified AR mutants from hormone refractory prostate cancer are capable of transcriptional activity. These observations suggest that loss of AR function is not a major cause of androgen ablation failure and that AR-negative prostate cancer cells do not have a significant growth or survival advantage. Instead, the available clinical and experimental evidence suggests that prostate cancer progression occurs through alteration of the normal androgen axis by misregulation of AR activity through signal transduction cascades, alteration in the expression of AR co-regulators, and mutations of AR that enable it to become transcriptionally active in response to other ligands than testosterone and DHT. Although serum androgens alone may not promote prostate carcinogenesis, androgen action and the functional status of AR are important mediators of prostate cancer progression. Low serum testosterone levels in men with newly diagnosed and untreated prostate cancer have been found to correlate with higher AR expression, increased capillary vessel density within the tumor, and higher Gleason score (Schatzl et al., 2002). Recent analysis of clinical prostate cancer specimens also collected from patients without preoperative treatment demonstrated that high AR expression correlated with lower recurrence-free survival and disease progression (Lee, 2003). The endocrinological treatment of prostate cancer primarily involves modulation of AR activity through deprivation of circulating testicular androgens by surgical castration or chemical castration with estrogen (diethylstilbestrol) and LHRH (luteinizing hormone-releasing hormone) agonists. The activity of AR may also be blocked by administration of anti-androgens, either alone or in combination with surgical or chemical castration (referred to as combined androgen blockade). Over 80% of patients show positive response to androgen ablation. However, patients with metastatic prostate cancer eventually experience disease progression in a median of 12 to 18 months after androgen deprivation therapy. The tumors of these patients are considered to be hormone refractory. Although these tumors are refractory in the sense that they have progressed despite a reduction in serum androgen and/or treatment with anti-androgens, the majority of these tumors are unlikely to be completely resistant to androgens. In 97% of patients with hormone refractory metastatic prostate cancer, exogenous androgen treatment results in disease flare and unfavorable response (reviewed in Fowler and Whitmore, 1982). Secondary therapy for patients with hormone refractory prostate cancer is also predominantly targeted at androgen production and AR function and includes administration of a secondary anti-androgen, inhibition of adrenal androgen production, and further LH (luteinizing hormone) inhibition with progesterone or estrogenic agents (Dawson and Vogelzang, 2000). Other cancers, like breast cancer, may also be AR positive (Moinfar et al., 2003). Androgen receptors are commonly expressed in breast ductal carcinoma in situ as well as in invasive breast carcinoma. A significant number of poorly differentiated breast carcinomas, while being ER (estrogen receptor)-negative and PR (progesterone receptor)-negative, are still AR-positive. Like prostate cancer, breast cancer is treated by hormone deprivation, which in this case, is achieved by mocking estrogen and estrogen receptor. With time, breast cancer finds ways to grow without the need for estrogen and becomes lethal. Breast cancers that become hormone refractory continue to express AR in the majority of cases. Although secondary hormonal therapy may also fails, the ability of therapies directed toward AR to provide positive therapeutic benefit suggests that AR activity is an important mediator of both prostate and breast cancer growth and survival.

In this regard, the evidence that steroidal receptors activate signal transduction cascades (Migliaccio et al., 1996) opened a new frontline for treatment of these cancers. It has been demonstrated that androgens, as well as estrogens, require Src/ras/erk pathway activation to stimulate DNA synthesis (Migliaccio et al., 2000). Such pathway activation occurs upon a direct interaction of steroidal receptors with the non receptor tyrosine-kinase Src. The sites crucial for these interactions have been identified.

Current Therapies

Non steroidal anti-androgens such as flutamide (Eulexin®), biclutamide (Casodex®) or nilutamide (Anandron®) have been used in hormone-responsive prostate cancer therapy. Similarly, anti-estrogen therapy by tamoxifen (Nolvadex®) or ICI 182,780 (Fulvestrant®) is commonly used in hormone-responsive breast cancer. Unfortunately, these and similar approaches frequently become ineffective because of development of drug resistance. In addition, these compounds have some undesirable side effects like increased risk of cardiovascular complications and, after chronic use, a small increased incidence of uterus carcinoma. Thus, there is an urgent need for treating prostate and mammary cancers in a more specific manner using non toxic alternative compounds. It was recently found that hormone- or growth factor-stimulated androgen receptor interacts with the tyrosine kinase Src, inducing prostate and mammary cancer cell proliferation "in vitro" (Castoria et al., 1999; Migliaccio et al., 1996; 2000; 2005).

WO 98/46250 discloses anti-estrogen phosphotyrosine or malonyltyrosine peptides mostly characterized by Leu motifs. The instant invention does not refer to such molecules.

WO 00/01813 discloses peptides derived from the aa. 234-391 of the human androgen receptor. Though some of disclosed peptides share some sequence similarity with the molecules of the invention, prior art document fails to disclose the antagonist activity of such peptides with respect to AR/Src binding/activation pathway. In addition, the peptides disclosed in WO 00/1813 have not been shown to reduce or block prostate or breast tumor cell growth. They have not been shown to exert a real and applicable anti-tumor activity.

Therefore, there is the need to provide peptides targeted to abolish the androgen receptor/Src association and the development of a new class of compounds for both prostate and breast cancer therapy.

SUMMARY OF THE INVENTION

The present invention overcomes pitfalls inherent in the prior art by providing novel compositions and methods to be used in treatment of prostate and breast cancers. The invention provides novel synthetic peptides, which exhibit anti-androgen receptor activity to be used in human prostate and/or breast cancer therapy or prevention. These peptides contain proline stretches, which have been implicated to play a major role in the interaction of AR with the SH3 domain of the tyrosine kinase Src (Migliaccio et al., 2000) and, potentially, other Src-family kinases. The SH3 domains are 50-70 amino acid long and can be often recognized in eukaryotic signal transduction and cytoskeletal proteins (Kay et al., 2000). They bind proline rich peptides, and, through such an interaction, play a major role in the regulation of kinase activity as well as the localization and substrate recognition. Each Src kinase family members has in its sequence a SH3 domain. The members of this family are nine (Williams et al, 1998) and others might be identified in the future. Agonist-occupied androgen and progesterone receptors have been reported to be able to interact with the SH3 domain of Src (Migliaccio et al., 2000; Boonyaratanakornkit et at, 2001). These associations probably remove the inhibitory action of the SH3 domain and trigger Src activation. Accordingly, the peptides disclosed in the present invention bind to SH3 domain of Src and prevent AR from interacting with Src and from activating signal transduction. It has been reported that androgen and estradiol receptors (ER) are associated under basal conditions (Migliaccio et al., 2005): when one of the two receptors is activated either by a steroid agonist or a growth factor, the two receptors interact with Src. Therefore, prevention of AR association with Src also prevents ER association with this kinase and Src activation by ER. As a consequence, the peptides disclosed herein also have an anti-estrogenic action.

The present invention provides an isolated or purified or partially purified peptide-derived molecule having the general formula:

X-[(Pro)$_n$-His-Pro-His-Ala-Arg-Ile-Lys]$_m$-Y   (S 1)(SEQ ID NO: 8)

wherein X is H, or an acetyl group or any natural amino acid or sequence of amino acids provided with a free or at least acetyl-derivatized $NH_2$ group; Y is an OH group or an $NH_2$ group or any amino acid or sequence of amino acids with a C-terminal carboxy-amide group; "n" is an integer from 1 to 10 and "m" is an integer from 1 to 3.

The peptide-derived molecule is able to inhibit or prevent the interaction of the androgen receptor (AR) with the SH3 domain of the tyrosine kinase Src.

The peptide-derived molecule has an anti-tumor activity in vitro or in vivo.

Additional variants of these peptides are also object of the present disclosure. Indeed, compounds derived by those described by formula S1, and able to fulfill similar biological functions can be devised (or derived) by achieving any kind of sequence duplication, triplication or, more in general, multimerization of the disclosed linear peptides. As an example, the peptides of the present invention may be modified according to the methods reported by Tam and co-workers (Tam and Spetzler J C, 1997) for the preparation of Multiple Antigen Peptides or by Mutter and co-workers for the preparation of Template-Assembled Synthetic Protein (TASP, Tuchscherer and Mutter, 1996).

The resulting molecules can be used for the purposes of the present application as trifluoroacetic salts, acetate salts, hydrochloric salts, sulphate salts or any other salt derived by dissolution in working buffers commonly used by those skilled in the art. Examples of polypeptide sequences disclosed in the present application are those listed in table 1:

TABLE I

| Sequence | SEQ. ID NO. |
|---|---|
| Ac-Pro-Pro-Pro-His-Pro-His-Ala-Arg-Ile-Lys-NH2 | (SEQ. ID NO. 1) |
| Ac-Pro-Pro-Pro-Pro-His-Pro-His-Ala-Arg-Ile-Lys-NH2 | (SEQ. ID NO. 2) |
| Ac-Pro-Pro-Pro-Pro-Pro-Pro-His-Pro-His-Ala-Arg-Ile-Lys-NH2 | (SEQ. ID NO. 3) |

TABLE I-continued

| Sequence | SEQ. ID NO. |
| --- | --- |
| Ac-Gly-Pro-Pro-Pro-Pro-Pro-Pro-Pro-Pro-His-Pro-His-Ala-Arg-Ile-Lys-NH2 | (SEQ. ID NO. 4) |
| Ac-Pro-Pro-Pro-Pro-Pro-Pro-Pro-His-Pro-His-Ala-Arg-Ile-NH2 | (SEQ. ID NO. 5) |
| Ac-His-Pro-His-Ala-Arg-Ile-Lys-NH2 | (SEQ. ID NO. 6) |
| Ac-His-Pro-Lys-Pro-Ala-Arg-Ile-Pro-His-Pro-NH2* | (SEQ. ID NO. 7) |

*The SEQ ID NO. 7 is shuffled sequence of SEQ. ID#NO. 1

In one embodiment, the invention concerns a composition comprising an isolated peptide between about four and about 30 or so amino acid residues in length, wherein the peptide includes within its sequence a peptide having the general formula S1 wherein each amino acid can be replaced by any derivative or analogue thereof.

In a second embodiment, the invention concerns a composition comprising an isolated peptide of between ten and about 50 or so amino acid residues in length, wherein the peptide includes within its sequence an amino acid sequence represented by:

Pro-Pro-Pro-His-Pro-His-Ala-Arg-Ile-Lys (SEQ. ID NO. 1)

wherein each amino acid can be replaced by any derivative or analogue thereof.

In a third embodiment, the invention concerns a composition comprising an isolated peptide of between twelve and about 50 or so amino acid residues in length, wherein the peptide includes within its sequence an amino acid sequence represented by:

Pro-Pro-Pro-Pro-Pro-His-Pro-His-Ala-Arg-Ile-Lys (SEQ. ID NO. 2)

wherein each amino acid can be replaced by any derivative or analogue thereof.

In a fourth embodiment, the invention concerns a composition comprising an isolated peptide of between fourteen and about 50 or so amino acid residues in length, wherein the peptide includes within its sequence an amino acid sequence represented by:

Pro-Pro-Pro-Pro-Pro-Pro-Pro-His-Pro-His-Ala-Arg-Ile-Lys (SEQ. ID NO. 3)

wherein each amino acid can be replaced by any derivative or analogue thereof.

In a fifth embodiment, the invention concerns a composition comprising an isolated peptide of between sixteen and about 50 or so amino acid residues in length, wherein the peptide includes within its sequence an amino acid sequence represented by:

Gly-Pro-Pro-Pro-Pro-Pro-Pro-Pro-His-Pro-His-Ala-Arg-Ile-Lys (SEQ. ID NO. 4)

wherein each amino acid can be replaced by any derivative or analogue thereof.

Preferred peptide compositions are those which either reduce or inhibit androgen receptor activity on cell growth. This reduction or inhibition has been shown by inventors to be accomplished by reducing or abolishing the AR interaction with Src kinase (SH3-binder peptide(s)). Preferably the peptide composition is from between seven and about 50 or so amino acid residues in length, and may include all such peptides having a length from ten amino acids up to and including those which have a length of about 55, 50, 45, 40, 35, 30, 25, 20, 15, 14, 13, or even 12 or 11 or so amino acids in length.

Exemplary peptides of about 10, 12, 14, 16 amino acids have been demonstrated to be particularly effective in reducing AR activity and DNA synthesis. Such exemplary peptides are disclosed in the sequence SEQ.ID NO.1 to SEQ.ID NO.6.

The peptides of the invention may optionally further comprise one or more amino acids at the amino-terminal, or one or more amino acids at the carboxy-terminal end of the disclosed peptides, or alternatively, may further comprise one or more amino acids at both ends of the disclosed anti-androgen motif. Such amino acids may be natural amino acids, amino acid derivatives, or substituted amino acids, and may extend the overall length of the primary amino acid sequence of the peptide 5, 10, 15, 20, even 25 or so additional amino acids at either the amino-terminal, the carboxy-terminal, or both ends of the AR motifs involved in the AR-Src interaction described herein.

As such the overall length of the preferred peptides may be up to including 50, 60, 70, 80, 90, or even 100 or so or more amino acids, so long as the peptide disclosed herein. Isolated peptides of from about 7 or about 10 and including up to and including about 100 or so amino acids, which comprise any of the sequences presented in SEQ.ID NO.1 to SEQ.ID NO.6 are preferred. The invention also contemplates that other sterically similar compounds may be formulated to mimic the key portions of the peptide structure and that these compounds may have the same use as the peptides of the invention in treating cancer and, in particular, prostate and breast cell carcinomas. Peptides of the invention may also be characterized as comprising at least 5 or more residues and include within their sequence at least two or more proline residues.

The peptides may be modified for use in therapeutics, for example by employing one or more D-amino acid(s) in place of L-amino acid(s), by adding groups for the N- or C-termini, such as by acylation, acetylation or amination. They can be also encapsulated within lipids, nano-capsules, lipid complexes and/or liposomes. Also the peptides can be incorporated in coating capsules for slow release.

The peptide-derived molecule of the invention may be used as anti-tumoral agent, preferably as anti-breast or anti-prostate cancer or against other cancers expressing androgen receptor alone or together with estradiol receptors.

It is an object of the invention a pharmaceutical composition comprising a pharmaceutically acceptable and effective amount of the peptide-derived molecule as above.

In a preferred embodiment in the composition the peptide is linked to a carrier molecule such as BSA or KLH and/or is comprised in a lipid composition such as a lipid particle, a nanocapsule, a liposome or lipid vesicles with a pharmaceutical excipient. Preferably the composition further comprises at least a second anti-cancer agent.

The peptides of the invention may also be used in the preparation of an antibody that specifically binds to an androgen receptor peptide, for the preparation of a medicament, also a vaccine.

Another object of the invention is an antibody able to recognize specifically the peptide-derived molecule.

A further aspect of the invention is a polynucleotide, a recombinant vector, a host cell comprising one or more of the peptide, polynucleotide or recombinant vector compositions disclosed herein. Each of them may be also used in the preparation of anti-cancer formulations.

The invention provides a kit comprising one or more of the disclosed anti-estrogen peptide compositions suitable for parental, intramuscular, intravenous injection or oral, nasal, or topical administration. The kit may contain one or more additional medicaments, a peptidomimetic or other agent. The peptides may be used in the preparation of a vaccine or an antibody.

In another embodiment the invention provides a method for reducing androgen receptor activity in a cell providing to the cell an amount of an anti-androgen peptide. The cell may be in culture, or comprised in an animal, which has been diagnosed with a cancer such as prostate or a breast carcinoma.

The invention also provides a method for reducing androgen receptor/Src association. A further embodiment of the invention provides a method for treating cancer in an animal. This method generally comprises identifying an animal with cancer such as prostate or breast cancer and administering to the animal a therapeutically effective amount of the anti-androgen peptide composition, which may be formulated in an excipient or a liposome or other lipid carrier, and may be prepared for administration through any conventional means of delivery.

The invention also provides a method of killing a tumor cell, preferably comprised within an animal, providing a therapeutically effective amount of an anti-estrogen peptide. It generally involves identifying an animal suspected of having cancer and administering to animal a therapeutically effective amount of the anti-androgen peptide. The formulation of the invention may also be used in the prevention of tumor cell development.

Composition of Anti-Androgenic Peptides

The present invention provides purified, and in preferred embodiments, substantially purified, proline-rich peptide derivatives which have anticancer properties. The term "purified peptides" as used herein, is intended to refer to a proteinic composition, wherein the peptide-rich peptides are purified to any degree relative to their naturally obtainable state. A purified peptide or peptide therefore also refers to a peptide or protein free from the environment in which it naturally occurs.

Generally, "purified" will refer to peptide composition that has been subjected to fractionation to remove various non peptide-derivative components.

Where the term "substantially purified" is used, it refers to a composition in which the peptide forms the major component of the composition, such as constituting about 50% of the proteins in the composition or more. In preferred embodiments, a substantially purified protein will constitute more than 60%, 70%, 80%, 90%, 95%, 99% or even 99.9% or more of the composition.

A polypeptide or protein that is "purified to homogeneity," as applied to the present invention, means that the polypeptide or protein has a level of purity where the polypeptide or protein is substantially free from other proteins and biological components. For example, a purified polypeptide will often be sufficiently free of other peptide components so that degradative sequencing may be performed successfully.

This invention is particularly concerned with proline-rich peptide derivatives such as isolated peptides of at least four or more residues in length, including those peptides up to and including about 50 or so amino acids, which comprise the amino acid sequences derived from the general formulae S1. Preferably, these peptides inhibit AR association to Src-SH3 domain, and are active in treating tumors and prostate and breast cancers in an affected animal, such as a human. The use of small peptides in therapeutics is preferred for various reasons. These include the low cost and ease of large scale preparation, and the reliability of the product. Also their biological properties are preferable, such as the ease with which peptides can penetrate tissues, their low immunogenicity, the fact that they present a smaller target for proteases thus affording longer bioavailability and, further, it is contemplated that they will function effectively in the prevention of AR-Src interaction and functioning as anti-androgen therapeutics.

However, although preferred for use in certain embodiments, there is no general requirement that the proline-rich, SH3-binder peptides always be provided in their most purified state. In this regard, any purification method well known to those of skill in the art can be employed so long as the sufficient level of peptide purity is achieved.

Synthetic peptides can be modified for example by employing one or more D-amino acids in place of L-amino acids, by adding groups to N- or C-termini, such as acylation or amination or by encapsulating the peptides within lipids, nanocapsules, lipid complexes and/or liposomes or in a biocompatible coating designed for slow-release. The present invention contemplates vaccines for use in both active and passive immunization. These vaccines may be prepared most readily from immunogenic peptides prepared in a manner disclosed herein.

Nucleic Acid Segments

The present invention also concerns DNA segments that can be isolated from virtually any source, that are free from total genomic DNA and that encode the whole or a portion of the novel peptides disclosed herein. Polynucleotides encoding the novel peptide species may be synthesized entirely in vitro using methods that are well known to those of skill in the art.

Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified anti-androgen peptide encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extra chromosomal DNA sequences, but also operon sequences and/or engineered gene segments that express, or may be adapted to express, proteins, polypeptides or peptides "Isolated substantially away from other coding sequences" means that the gene of interest, in this case, an anti-androgen polypeptide gene, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode an anti estrogen peptide species that includes within its amino acid sequence any of the amino acid sequences set forth in general formula Si or in the examples of polypeptides SEQ.ID NO.1 to SEQ.ID NO.6. More preferably, the DNA sequence comprises a nucleic acid sequence that encodes an anti-androgen peptide species that includes within its amino acid sequence an at least ten amino acid sequence contiguous to those set forth in general formula S1 or in the peptides SEQ.ID NO.1 to SEQ.ID NO.6

The term "a sequence essentially as set forth in general formula Si or in the examples of polypeptides SEQ.ID NO.1 to SEQ.ID NO.6" means that the sequence substantially corresponds to a portion of the sequence of general formula Si or in the examples of polypeptides SEQ.ID NO.1 to SEQ.ID NO.6 and has relatively few amino acids that are not identical to, or a biologically functional equivalent of, the amino acids of any of these sequences. The term "biologically functional equivalent" is well understood in the art and is further defined in detail herein. Accordingly, sequences that have between about 70% and about 80%, or more preferably between about 81% and about 90%, or even more preferably between about 91% and about 99% amino acid sequence identity or functional equivalence to the amino acids of any one of SEQ.ID NO.1 to SEQ.ID NO.6.

Accordingly, sequences that have between about 70% and about 80%, or more preferably between about 81% and about 90%, or even more preferably between about 91% and about 99% amino acid sequence identity or functional equivalence to the amino acids of any one of SEQ.ID NO.1 to SEQ.ID NO.6, will be sequences that are "essentially as set forth in any one of SEQ.ID NO.1 to SEQ.ID NO.6.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological anti-androgen activity where peptide expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the whole or a portion of the peptide sequence disclosed in SEQ.ID NO:1 and/or SEQ.ID NO:2 or that are identical to or complementary to DNA sequences which encode any of the peptides disclosed in SEQ.ID NO:1 and SEQ.ID NO: 2. For example, DNA sequences such as about 30 nucleotides, and that are up to about 10,000, about 5,000, about 3,000, about 2,000, about 1,000, about 500, about 200, about 100, about 50, and about 30 base pairs in length (including all the intermediate lengths) are also contemplated to be useful.

It will also be understood that this invention is not limited to the particular nucleic acid sequences which encode peptides of the present invention, or which encode the amino acid sequence of SEQ.ID NO.1 to SEQ.ID NO.6.

Recombinant vectors and isolated DNA segments may therefore variously include the peptide coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site directed mutagenesis techniques, e.g., to introduce improvements to the antigenicity of the protein or to test mutants in order to examine activity at the molecular level.

If desired, one may also prepare fusion proteins and peptides, e.g., where the peptide coding regions are aligned within the same expression unit with other proteins or peptides having desired functions, such as for purification or immunodetection purposes.

Recombinant vectors form further aspects of the present invention. Particularly useful vectors are contemplated to be those vectors in which the coding portion of the DNA segment, whether encoding a full-length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon.

DNA Segments as Hybridization Probes and Primers

In addition to their use in directing the expression of the peptides of the present invention, the nucleic acid sequences contemplated herein also have a variety of other uses.

For example, they also have utility as probes or primers in nucleic acid hybridization embodiments.

The ability of such nucleic acid probes to specifically hybridize to an anti-androgen peptide-encoding sequences will enable them to be of use in detecting the presence of complementary sequences in a given sample. However, other uses are envisioned, including use of sequence information for the preparation of mutant species primers, or primers for use in preparing other genetic constructions.

Nucleic acid molecules having sequence regions consisting of contiguous nucleotide stretches of 10-14, 15-20, 30, 50, or even of 100-200 nucleotides or so, identical or complementary to the DNA sequences which encode the disclosed polypeptides, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length of complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.).

Recombinant Vectors and Polypeptide Expression

The invention also discloses and claims compositions comprising any of disclosed anti-androgen peptide. The composition may be comprised within one or more host cells which express a nucleic acid segment encoding an anti-androgen peptide, recombinant host cells which express the peptides or fusion proteins comprising the peptides, cell suspensions, extracts, inclusion bodies, or tissue cultures or culture extracts which contain the disclosed anti-androgen peptides, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing anti-androgen peptides are well-known to those of skill in the art of protein isolation and purification. In certain embodiments, the anti-androgen peptides may be purified, concentrated, admixed with other reagents, or processed to a desired final form. Preferably, the composition will comprise from about 1% to about 90% by weight of the anti-androgen peptide, and more preferably from about 5% to about 50% by weight.

In a preferred embodiment, the anti-androgen peptide compositions of the invention may be prepared by a process which comprises the steps of culturing a host cell which expresses an anti-androgen peptide under conditions effective to produce such a peptide, and then obtaining the peptide from the cell. The obtaining of such an anti-androgen peptide may further include purifying, concentrating, processing, or admixing the polypeptide within one or more reagents. Preferably, the anti-androgen peptide is obtained in an amount of from between about 1% to about 90% by weight, and more preferably from about 5% to about 70% by weight, and even more preferably from about 10% to about 20% to about 30%, or even to about 40% or 50% by weight.

The invention also relates to a method of preparing an anti-androgen peptide composition. Such a method generally involves the steps of culturing a host cell, which expresses an anti-androgen peptide under conditions effective to produce the peptide, and then obtaining the polypeptide so produced.

The recombinant plasmid vectors of the invention may be used to transform other suitable bacterial or eukaryotic cells to produce the anti-androgen polypeptides of the invention.

Eukaryotic host cells including NIH3T3, COS7, and CAOV3, as well as yeast cells are contemplated to be particularly useful in the preparation of the peptide species.

Likewise, prokaryotic host cells including Gram-negative cells such as *E. coli, Pseudomonas* spp. and related Enterobacteraceae and the like are all contemplated to be useful in the preparation of the anti-androgen peptides of the invention.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding an anti-androgen peptide in its natural environment. Such promoters may include promoters normally associated with other genes, and/or promoters isolated from any bacterial, viral, or eukaryotic cell. Preferred eukaryotic cells are animal cells, with mammalian cells, particularly human cells, being most preferred. Naturally, it will be important to employ a promoter that effectively directs the expression of the DNA segment in the cell type, tissue, organism, animal, or recombinant host cell chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides.

Therapeutic and Diagnostic Kits

Therapeutic kits of the present invention are kits comprising disclosed proline-rich peptide containing protein, peptide, inhibitor, gene, vector or other peptide binding protein effector. Such kits will generally contain, in suitable container means, a pharmaceutically acceptable formulation of disclosed proline-rich peptide containing protein, peptide, inhibitor, gene, vector or other peptide binding protein effector or vector expressing any of the foregoing in a pharmaceutically acceptable formulation, optionally comprising other anti-cancer agents. The kit may have a single container means, or it may have distinct container means for each compound.

When the components of the kit are provided in one or more liquid solutions, the liquid solution is an aqueous solution, with a sterile aqueous solution being particularly preferred. The aforementioned compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means. Where a second anti-cancer therapeutic is provided, the kit will generally contain a second container. The kits may also comprise other containers for acceptable diluent.

Methods of Nucleic Acid Delivery and DNA Transfection

In certain embodiments, it is contemplated that the nucleic acid segments disclosed herein will be used to transfect appropriate host cells. Technology for introduction of DNA into cells is well-known to those of skill in the art. Four general methods for delivering a nucleic segment into cells can be considered:
(1) chemical methods (Graham and VanDerEb, 1973);
(2) physical methods such as microinjection (Capecchi, 1980), electroporation (Wong and Neumann, 1982; Frommm et al., 1985) and the gene gun (Yang et al., 1990);
(3) viral vectors (Clapp, 1993; Eglitis et al., 1988; Eglitis and Anderson, 1988); and
(4) receptor-mediated mechanisms (Curiel et al., 1991; Wagner et al., 1992).

Liposomes and Nanocapsules

In certain embodiments, the inventor contemplates the use of liposomes and/or nanocapsules for the introduction of peptide compositions into host cells. Such formulations may be preferred for the introduction of pharmaceutically-acceptable formulations of the polypeptides, pharmaceuticals, and/or antibodies disclosed herein. The formation and use of liposomes is generally known to those of skill in the art (see for example, Couvreur et at, 1977, which describes the use of liposomes and nanocapsules in the targeted antibiotic therapy of intracellular bacterial infections and diseases). More recently, liposomes were developed with improved serum stability and circulation half-times (Gabizon and Papahadjopoulos, 1988; Allen and Choun, 1987).

The drawings form part of the present specification and are included to further demonstrate certain aspects of the present invention. The invention may be better understood by reference to one or more of these drawings in combination with the detailed description of specific embodiments presented herein.

FIG. 1A. DNA synthesis inhibition of human prostate cancer cells by Src-SH3 binder peptide modeled from AR (SEQ.ID NO.1). LNCaP cells derived from human prostate cancer were grown in phenol red-free medium added with charcoal-treated serum as previously described (Migliaccio et al., 2000) and treated for 24 hrs with 10 nM R1881 synthetic androgen alone or in the presence of a 1000-fold excess of the anti-androgen Casodex or 1 nM of the SH3-binder peptide (SH3, SEQ.ID NO.1) or 1 nM Ss (shuffled sequence: SEQ.ID NO.7) peptide. At the end of hormone treatment BrdU incorporation in cells untreated (control) or treated with R1881 alone (R1881) or in the presence of casodex (Cdx) or SH3 binder peptide (SH3, SEQ.ID NO.1) or shuffled sequence of peptide SEQ.ID NO.1 (Ss, SEQ.ID NO.7) was assayed as reported (Castoria et al., 1999). Data are presented as percentage of cells incorporating BrdU, averaged from 6 experiments.

FIG. 1B. DNA synthesis inhibition of estradiol-stimulated human breast cancer cells by SH3 binder peptides derived from AR (SEQ.ID NO.1). MCF-7 cells derived from human breast cancer were maintained for 3 days in phenol red-free medium containing charcoal-treated serum as previously described and treated for 24 hrs with 10 nM 17ẞ estradiol alone or in the presence of a 1000-fold excess of the anti-estrogen ICI 182,780 or 1 nM of the SH3-binder peptide SEQ.ID NO.1 or the shuffled sequence (Ss, SEQ.ID NO.7) of peptide SEQ ID NO.1. At the end of the hormone treatment BrdU incorporation in the cells untreated (control) or treated with estradiol alone (E2) or in the presence of ICI 182,780 (ICI) or AR-derived (SH3) or Ss peptide was assayed. Data are reported as percentage of cells incorporating BrdU, averaged from 6 experiments.

FIG. 1C. DNA synthesis inhibition of EGF-stimulated human prostate cancer cells by SH3 binder peptide modeled from AR (SEQ. ID NO.1). LNCaP cells were grown in phenol red-free medium added with charcoal-treated serum as previously described and treated for 24 hrs with 100 ng/ml EGF alone or in the presence of a 10 μM of the anti-estrogen ICI 182,780 or 1 nM of the AR-derived (SH3-binder) peptide (SEQ.ID NO.1) or the shuffled sequence of peptide SEQ.ID NO.1 (SEQ.ID NO.7). At the end of the growth factor treatment BrdU incorporation in the cells untreated (control) or treated with EGF alone (EGF) or in the presence of ICI 182,780 (ICI) or the SH3-binder (SH3) or the shuffled sequence of peptide SEQ. ID NO.1 (Ss) was assayed. Data are reported as percentage of cells incorporating BrdU.

FIG. 1D. DNA synthesis inhibition of EGF-stimulated human breast cancer cells by SH3 binder peptides modeled from AR (SEQ. ID NO.1). MCF-7 cells were grown in phenol red-free medium added with charcoal-treated serum as previously described and treated for 24 hrs with 100 ng/ml EGF alone or in the presence of a 10 μM of the anti-estrogen ICI 182,780 or 1 nM of the AR-derived (SH3-binder) peptide or the shuffled sequence of peptide SEQ ID NO. 1(SEQ.ID. NO.7). At the end of the growth factor treatment, BrdU incorporation in the cells untreated (control) or treated with EGF alone (EGF) or in the presence of ICI 182,780 (ICI) or SH3-binder (SH3) or shuffled sequence of peptide SEQ.ID NO.1 (Ss) was assayed. Data are reported as percentage of cells incorporating BrdU.

Figure 2A:
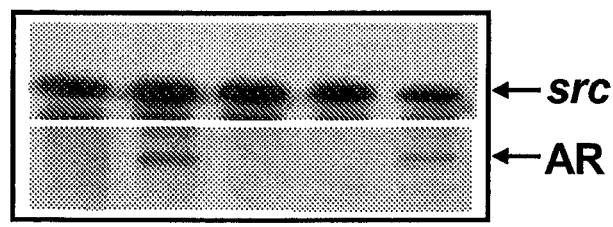

FIG. 2A. Inhibition of androgen-stimulated AR association with Src by the AR-derived (Src-SH3 binder) peptide (SEQ.ID NO.1). Human prostate cancer LNCaP cells were left unstimulated or stimulated for 2 min with 10 nM R1881 alone or in the presence of 1000-fold excess of Casodex or 1 nM of the SH3-binder peptide or the shuffled sequence of peptide SEQ.ID NO.1 (SEQ.ID NO.7). Cell lysates were incubated with anti-Src antibodies, and the immunoprecipitated proteins resolved on SDS-PAGE and transferred onto nitrocellulose filters. Filters were then blotted with either anti-Src or anti-human AR antibodies to detect AR associated with Src. Immunocomplexes were revealed using ECL detection kit. Lane 1: unstimulated cells; lane 2: R1881 treated cells; lane 3: cells treated with R1881 in the presence of Casodex (Cdx); lane 4: cells treated with R1881 in the presence of the SH3 binder peptide (SH3, SEQ.ID NO.1); lane 5: cells treated with R1881 in the presence of the shuffled sequence of peptide SEQ.ID NO.1 (Ss, SEQ.ID NO.7).

Figure 2B:
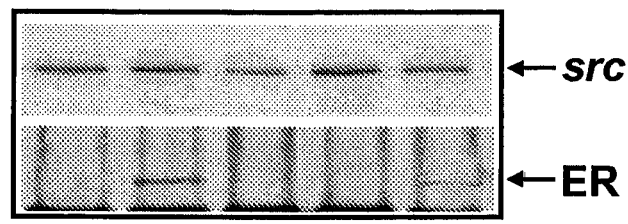

FIG. 2B. Inhibition of estrogen-stimulated AR association with Src by the AR-derived Src-SH3 binder peptide (SEQ.ID NO.1). Human breast cancer MCF-7 cells were left unstimulated or stimulated for 2 min with 10 nM 17ẞ estradiol alone or in the presence of a 1000 fold excess of ICI 182,780 or 1 nM of the SH3 binder peptide or the shuffled sequence of peptide SEQ.ID NO.1 (SEQ.ID NO.7). Cell lysates were incubated with anti-Src antibodies, immunoprecipitated proteins were resolved on SDS-PAGE and transferred onto nitrocellulose filters. Filters were then blotted with either anti-Src or anti-human AR antibodies to detect AR associated with Src. Immunocomplexes were revealed using ECL detection kit. Lane 1: unstimulated cells; lane 2: estradiol (E2) treated cells; lane 3: cells treated with E2 in the presence of ICI 182,780 (ICI); lane 4: cells treated with E2 in the presence of SH3 binder peptide (SH3); lane 5: cells treated with estradiol in the presence of the shuffled sequence of peptide SEQ.ID NO.1 (Ss)

Figure 3A:
Figure 3A:

FIG. 3A. Inhibition of androgen-induced cyclin D1 expression by AR-derived Src-SH3 binder peptide (SEQ.ID NO.1). Quiescent MCF-7 and LNCaP cells were left untreated or treated for 8 hrs with 10 nM R1881 alone or in the presence of 5 µM PI3-kinase inhibitor LY294,002 or 1 nM AR-derived SH3 binder or the shuffled sequence of peptide SEQ.ID NO.1 (SEQ.ID. NO.7). Protein from cell lysates were resolved on SDS-PAGE, then transferred to nitrocellulose filters. Endogenous Cyclin D1 was revealed using appropriate antibodies. Lanes 1: unstimulated cells; lanes 2: R1881 treated cells; lanes 3: cells treated with R1881 in the presence of LY294,002 (LY); lanes 4: cells treated with R1881 in the presence of AR-derived (SH3-binder) peptide (SH3); lane 5: cells treated with R1881 in the presence of the shuffled sequence of peptide SEQ.ID NO.1 (Ss).

Figure 3B:
Figure 3B:

FIG. 3B. Inhibition of estrogen-induced cyclin D1 expression by AR-derived SH3 binder peptide (SEQ.ID NO.1). Quiescent MCF-7 and LNCaP cells were left untreated or treated for 8 hrs with 10 nM 17ß estradiol alone or in the presence of 5 µM PI3-Kinase inhibitor LY294,002 or 1 nM of the SH3 binder or the shuffled sequence of peptide SEQ.ID NO.1 (SEQ.ID NO.7). Protein from cell lysates were resolved on SDS-PAGE, then transferred to nitrocellulose filters. Endogenous Cyclin D1 was revealed using appropriate antibodies. Lanes 1: unstimulated cells; lanes 2: estradiol treated cells; lanes 3: cells treated with estradiol in the presence of LY294,002 (LY); lane 4: cells treated with estradiol in the presence of SH3-binder peptide (SH3); lane 5: cells treated with estradiol in the presence of the shuffled sequence of peptide SEQ.ID NO.1 (Ss).

FIG. 4A. Ineffectiveness of AR-derived (SH3 binder) peptide (SEQ.ID NO.1) on androgen receptor regulated gene transcription in prostate cancer (LNCaP cells). LNCaP cells were transfected with a reporter gene encoding the luciferase gene under the control of an androgen responsive element (ARE 3416) (Castoria et al., 2003). Six hrs after transfection, cells were kept for further 24 hrs in the absence or in presence of 10 nM R1881 alone or with a 1000 fold excess of Casodex or with 1 nM SH3 binder peptide (SEQ.ID NO.1) or 1 nM shuffled sequence of peptide SEQ.ID NO.1 (SEQ.ID. NO.7). Luciferase activity was then assayed in cell lysates. Bar1: unstimulated cells; Bar 2: R1881 treated cells; Bar 3: cells treated with R1881 in the presence of Casodex (Cdx); Bar 4: cells treated with R1881 in the presence of the SH3 binder peptide (SH3); Bar 5: cells treated with R1881 in the presence of the shuffled sequence of peptide SEQ.ID NO.1 (Ss).

FIG. 4B. Ineffectiveness of AR-derived (SH3 binder) peptide (SEQ.ID NO.1) on estrogen receptor regulated gene transcription in breast cancer (MCF-7 cells). MCF-7 cells were transfected with a reporter gene encoding the luciferase gene under the control of an estrogen responsive element (vt-tk-LUC) (Castoria et al., 2003). Six hrs after transfection, cells were kept for further 24 hrs in the absence or in presence of 10 nM 17ß-estradiol (E2) alone or with a 1000 fold excess of ICI 182,780 or with 1 nM SH3 binder peptide (SEQ.ID NO.1) or 1 nM shuffled sequence of peptide SEQ.ID NO.1 (SEQ.ID. NO.7). Luciferase activity was then assayed in cell lysates. Bar 1: unstimulated cells; Bar 2: E2 treated cells; Bar 3: cells treated with E2 in the presence of ICI 182,780 (ICI); Bar 4: cells treated with E2 in the presence of the SH3 binder peptide (SH3); Bar 5: cells treated with E2 in the presence of the shuffled sequence of peptide SEQ ID NO.1(Ss).

Figure 5:
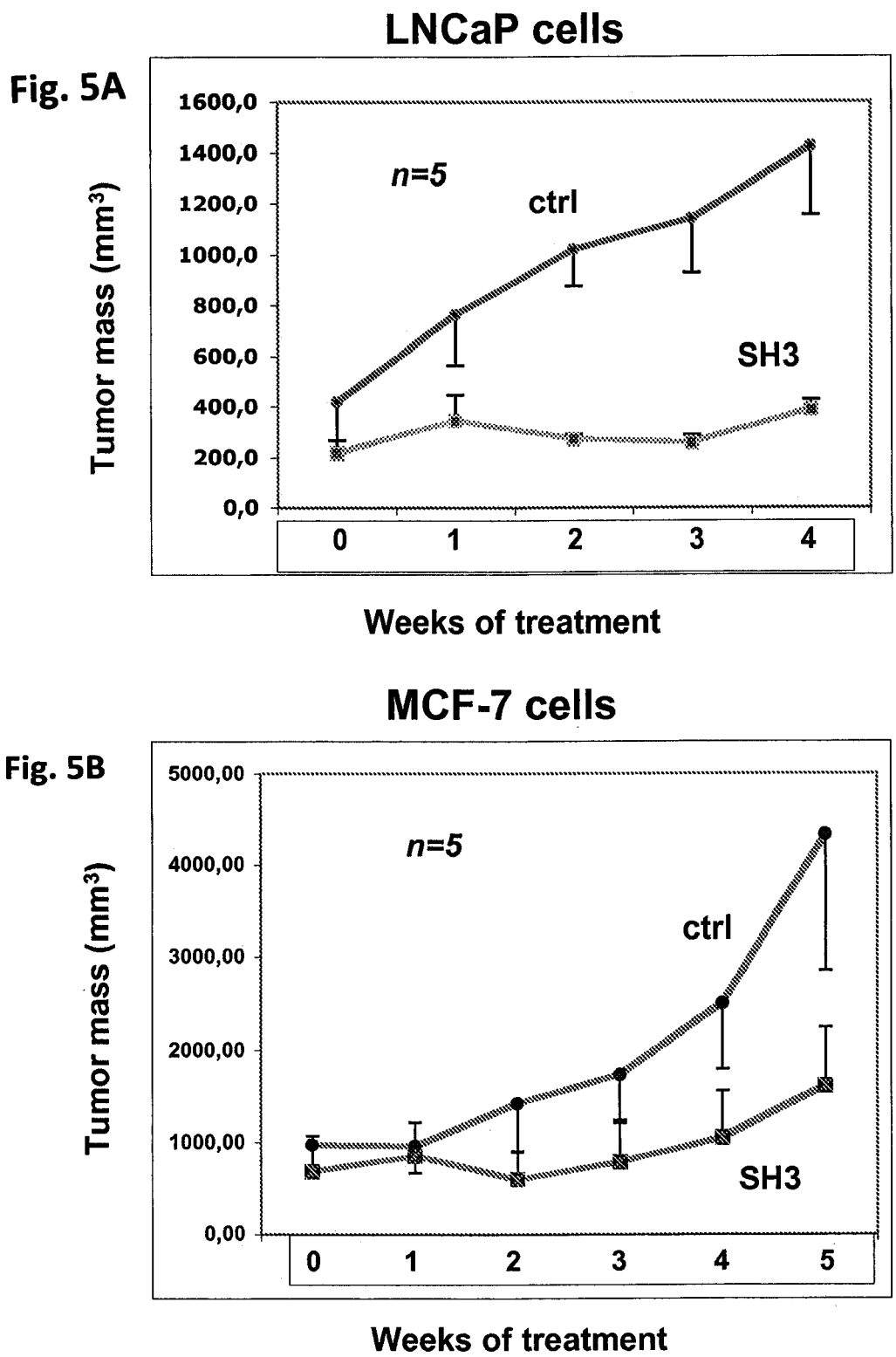

FIG. 5A Effect of SH3-binder peptide on human prostate cancer cells in vivo. LNCaP prostate cancer cells were grown subcutaneously in nude male mice. After tumor reached the size of 200-400 $mm^3$, mice were treated with intra-peritoneal injection of 200 µl of control (ctrl) solution (circles) or the same solution containing 2 µM of SH3 (SH3) binder peptide SEQ.ID NO.1 (squares). Treatment started at beginning of week 0 and peptides were given in alternate days for 4 weeks, using 5 animals per group.

FIG. 5B Effect of SH3-binder peptide on human breast cancer cells in vivo. MCF-7 human breast cancer cells were grown subcutaneously in nude male mice. When tumors were about 1000 $mm^3$ in size, mice were treated with intraperitoneal injection of 200 µl of control solution (ctrl, circles) or 200 µl of the same solution containing 2 µM of the SH3 binder peptide SEQ.ID NO.1 (SH3, squares). Treatment started at beginning of week 0 and peptides were given in alternate days for 5 weeks, using 5 animals per group FIG. 6A. Effect of SH3-binder peptide on Ki-67 antigen expression and apoptosis in human prostate cancer cells. LNCaP cell xenografts in male nude mice are the same as the one used in the experiment presented in FIG. 5A. At the end of the treatment, tumor specimens were assayed for Ki-67 antigen expression and apoptosis. The left panel shows the expression of Ki-67 antigen as percentage of Ki-67 positive cells in untreated (ctrl) and SEQ.ID NO.1 peptide treated (SH3) mice. The right panel shows the TUNEL assay positive cells observed in representative fields.

FIG. 6B. Effect of SH3-binder peptide on Ki-67 antigen expression and apoptosis in human breast cancer cells. MCF-7 cells xenografts in male nude mice are the same as the one used in the experiment of FIG. 5B. At the end of treatment tumor specimens were assayed for Ki-67 antigen expression and apoptosis. The left panel shows the expression of Ki-67 antigen as percentage of Ki-67 positive cells in untreated (ctrl) and SEQ.ID NO.1 peptide treated (SH3) mice. The right panel shows the TUNEL assay positive cells observed in representative fields.

EXAMPLES

The following examples are included to demonstrate preferred embodiments of the invention. However, those of skill in the art should, in light of the present disclosure, appreciate that many changes can be made in the specific embodiments which are disclosed and still obtain a like or similar result without departing from the spirit and scope of the invention.

Example 1: Preparation of AR-Derived Src-SH3 Binder Peptide (SEQ. ID. No. 1) by Chemical Synthesis Peptides 1 through 4 can be conveniently manually prepared by applying the solid phase method (Bodansky M and Bodansky A, 1995) and the Fmoc/tBu (Fmoc: 9-fluorenyl-methoxycarbonyl) chemistry that is largely described in the scientific literature (Carpino and Han, 1972; Fields and Noble, 1990) and is well known to those skilled in the art. To expedite and facilitate the preparation, automatic multiple peptide synthesizers can be utilized. Any kind of chemical method or mechanic synthesizer with single or multiple channels can be also conveniently used to carry out the synthesis, without affecting the biological properties of the final compounds.

The synthesis of the peptide is performed on a scale of 50 µmoles using a resin suitably derivatized with a RINK linker capable to give C-terminal amide peptides (Rink, 1987). One of such resins is the product 4-(2',4'-Dimethoxyphenyl-Fmoc-aminomethyl)-phenoxy resin, 100-200 mesh; copoly-styrene 1% Di-vinylbenzene), substitution 0.50 mmol/g (Novabiochem cat. N. 01-64-5026), also known as RINK AMIDE resin to those skilled in the art. An amount of 100 mg of resin is used. The resin is placed in a 5 ml polypropylene reaction vessel (RV) endowed with a filtration septum at the bottom (Shimadzu Corp. cat. N. 292-05250-02). In a typical protocol, the resin is swollen for 10 minutes under stirring and then rinsed several times (at least 4) with 1.0 mL of dry N,N-dimethylformamide (DMF, Peptide synthesis grade, LabScan, cat. N. H6533) by removing the solvent from the bottom applying a slight vacuum. The resin is then treated with 1.0 mL of a 20% v/v solution of piperidine (BIOSOLVE LTD, cat. N. 16183301) in DMF for 15 minutes at room temperature under stirring to remove the initial Fmoc group and washed several times (at least 4) with 1.0 mL of dry DMF for 2 minutes to remove the excess of reagent.

Then the following 6 steps are carried out subsequently:
1. 250 µmoles (117 mg) of Fmoc-L-Lys(Boc)-OH (Novabiochem, cat. 04-12-1026) are dissolved in 500 µL of dry DMF.
2. The protected aminoacid is preactivated with 400 µL of solution A and 400 µL of solution B for 4 minutes under stirring at room temperature, where:
Solution A Contains:
  0.5 M 2-(1H-Benzotriazol-yl)-1,1,3,3-tetramethyl-uronium tetrafluoroborate (TBTU, >99%, Chem-Impex Intl, cat. N. 02056) and 0.5 M of 1-Hydroxybenzotriazole (HOBt, SIGMA-ALDRICH, cat. H2006) in DMF.
Solution B Contains:
  1 M Di-isopropyl-ethylamine (DIEA, SIGMA-ALDRICH, cat. N.D-3887) in DMF.
3. The solution is transferred on to the resin and stirred for 30 minutes.
4. The reagent is removed under vacuum and the resin washed 4 times with 1.0 mL of dry DMF.
5. The resin is again treated with 1.0 mL of 20% v/v piperidine in DMF for 15 minutes at room temperature under stirring to remove the N-terminal Fmoc.
6. The resin is washed 3 times with 1.0 mL of DMF.

Steps 1 through 6 are then repeated, by changing in step 1 the corresponding protected amino acid requested in the sequence. The protected derivatives used are reported in the following Table II.

TABLE II

Common protected amino acids used for the chemical synthesis of peptide SEQ. ID NO. 1 and amounts required.

| AA | Protected deriv. | Amount | Code |
|---|---|---|---|
| Ile | Fmoc-L-Ile-OH | 88 mg (250 µmol) | Novabiochem, cat. 04-12-1024 |
| Arg | Fmoc-L-Arg(Pbt)-OH | 161 mg (250 µmol) | Novabiochem, cat. 04-12-1145 |
| Ala | Fmoc-L-Ala-OH | 78 mg (250 µmol) | Novabiochem, cat. 04-12-1006 |
| His | Fmoc-L-His(Trt)-OH | 155 mg (250 µmol) | Novabiochem, cat. 04-12-1065 |
| Pro | Fmoc-L-Pro-OH | 84 mg (250 µmol) | Novabiochem, cat. 04-12-1031 |
| Lys | Fmoc-L-Lys(Boc)-OH | 117 mg (250 µmol) | Novabiochem, cat. 04-12-0069 |

Fmoc-L-Lys(Boc)-OH indicates the protected lysine derivative: N-α-Fmoc-N-ε-t-Boc-L-lysine and the symbol "t-Boc", indicates the protecting group t-butyloxycarbanyl;
Fmoc-L-Ile-OH indicates the protected isoleucine derivative: N-α-Fmoc-L-isoleucine;
Fmoc-L-Arg(Pbf)-OH indicates the protected arginine derivative: N-α-Fmoc-N$^G$-2,2,4,6,7-pentamethyldihydrobenzofuran-5-sulfonyl-L-arginine;
Fmoc-L-Ala-OH indicates the protected alanine derivative: N-α-Fmoc-L-alanine;
Fmoc-L-His(Trt)-OH indicates the protected histidine derivative: N-α-Fmoc-N-im-trityl-L-histidine and the symbol "trityl", indicates the protecting group t-phenylmethyl;
Fmoc-L-Pro-OH indicates the protected proline derivative: N-α-Fmoc-L-proline.

After removal of the last Fmoc group, the resin is acetylated by treatment with a 1.0 M solution in dry DMF of Acetic Anhydride (Fluka, cat. 45830), containing 1.0 M DIEA for 30 minutes at room temperature under stirring. After extensive rinsing with DMF, the resin is submitted to the following washings:

| Solvent | N° of washes | Volume (mL) |
|---|---|---|
| DMF | 3 | 4.0 |
| MeOH* | 3 | 4.0 |
| Et$_2$O** | 3 | 4.0 |

*Methanol (MeOH, LabScan, cat. N. A3513),
**Ethyl Ether (Et$_2$O, LabScan, cat. N. A3509E).

The resin is dried applying a Nitrogen stream and then weighted. The final weight of the resin is 280.0 mg.

3.0 mL of a TFA-H$_2$O-TIS (100:5:5, v/v/v) mixture (TIS, tri-iso-propylsilane, SIGMA-ALDRICH cat. N. 23,378-1) are freshly prepared and added to the resin. After stirring for 3 hours, the resin is filtered off and the acidic solution is directly collected in a 15 ml polypropylene tube containing 15 mL of cold Et$_2$O. The white precipitate is separated by centrifugation at 3000 rpm for 10 minutes and the organic solvents are discarded. The precipitate is washed once with 5.0 mL of cold Et$_2$O and after centrifugation is dissolved in 2.0 mL of deionized H$_2$O and lyophilized. The white solid is weighted: 102 mg.

The lyophilized peptide can be conveniently purified by reverse phase chromatography using commercially available High Performance Liquid Chromatography (HPLC) systems, such as, for example, the LC-8 system provided by Shimadzu Corp., equipped with commercially available preparative reversed phase C18 columns, such as the Jupiter 25×2.1 cm ID C18 columns (Phenomenex cat. N. 00G-4053-P0) provided by Phenomenex. Typical gradients for the peptide purification make use of solvents such as deionized H$_2$O, 0.1% trifluoroacetic acid (TFA, Sigma-Aldrich, Cat N. 91700) and acetonitrile (CH$_3$CN, LabScan, Cat. NO C2503, 0.1% TFA and are from a typical concentration of 5% CH$_3$CN, 0.1% TFA to 60% over 35 minutes with a typical operating flow rate of 20 mL/min. These methods are very well known to those skilled in the art and will provide purified peptides with purity levels of up to 95-99% as determined by analytical HPLC analysis on a commercially analytical RP18 columns, such as the Phenomenex Jupiter column, 250×4.6 mm ID RP-18 (Phenomenex cat. N. 00G-4053-E0). Gradients are from 5% $CH_3CN$, 0.1% TFA to 60% over 35 minutes, with a typical flow rate of 1.0 mL/min. Monitoring is typically achieved by using UV-vis detector implemented on to the HPLC systems and set at a typical wavelength of 214 nm.

The final peptide is conveniently characterized by mass spectrometry methods, such as MALDI-TOF and ESI-MS. In a typical example, the experimental molecular weight (MW) determined with an ESI-MS mass spectrometer is 1189.5 atomic mass units (amu), in agreement with the theoretical value of 1189.68 amu (monoisotopic species).

Example 2: "In Vitro" Anti Tumor Effect of the AR-Derived Src-SH3 Binder Peptide SEO. ID NO.1

It has been shown that treatment of human prostate cancer LNCaP with 10 nM R1881 synthetic androgen strongly stimulates DNA synthesis. Therefore, LNCaP cells are routinely grown in 5% $CO_2$ in air in RPMI 1640 medium (GIBCO) supplemented with phenol-red, 2 mM L-glutamine (GIBCO), penicillin (100 U/ml), gentamicin (50 µl/ml), insulin (Humulin I 0.2 U.I/ml, Roche) and 10% fetal calf serum. Cells are then seeded onto gelatine-precoated coverslips at about 40% confluence and maintained in phenol red-free RPMI-1640 containing insulin and charcoal stripped calf serum to assure minimal to no steroid contamination (Shi et al., 1994) for 3 days. LNCaP cells are then treated for 24 hrs with 10 nM of the synthetic androgen R1881 (Astra-Zeneca) alone or in the presence of a 1000-fold molar excess of the anti-androgen Casodex (Astra-Zeneca) or with the indicated peptides.

Results presented in FIG. 1A, averaged from six different assays show that androgen increases from 20 to 54% BrdU incorporation rate. The hormone stimulated incorporation is strongly reduced (25% of residual BrdU incorporation) by SH3 binder peptide at a concentration of 1 nM (SH3). The effect of SH3 peptide was compared with that of the pure anti-androgen Casodex, which reduced by a similar extent DNA synthesis (21% of residual BrdU incorporation). A synthetic peptide corresponding to the shuffled sequence of SEQ.ID NO.1 (SEQ.ID NO.7) was also used (Ss). Addition of this peptide during androgen stimulation of cells has only a negligible inhibitory effect on hormone-dependent DNA synthesis (48% of residual BrdU incorporation). In addition to the above mentioned peptides, peptides SEQ.ID NO.2-SEQ.ID NO.4 were tested. The inhibitory effect was not stronger than that of the peptide SEQ.ID NO.1.

The effect of peptide SEQ.ID NO.1 was also tested on estradiol-stimulated DNA synthesis of MCF-7 human breast cancer cells. MCF-7 cells were grown in 5% $CO_2$ in air in Dulbecco modified Eagle medium (DMEM, GIBCO) supplemented with phenol-red, 2 mM L-glutamine (GIBCO), penicillin (100 U/ml), gentamicin (50 µl/ml), hydrocortisone 3.75 ng/ml, insulin (Humulin I 0.2 U.I/l, Roche) and 5% fetal calf serum. Cells are then seeded onto gelatine-precoated coverslips at about 40% confluence and maintained in phenol red-free DMEM containing insulin and charcoal stripped calf serum for 3 days. MCF-7 cells are then treated for 24 hrs with the 10 nM 17ß estradiol (SIGMA, Mo.) alone or in the presence of a 1000-fold molar excess of anti-estrogen ICI 182,780 (Astra-Zeneca) or with the indicated peptides.

Results presented in FIG. 1B, averaged from six different assays show that estradiol ($E_2$) increases from 8 to 61% BrdU incorporation rate. The hormone stimulated incorporation is significantly reduced (23% of residual BrdU incorporation) by the SH3 binder peptide (SH3) at a concentration of 1 nM. The effect of SH3 peptide is comparable with that of pure anti-estrogen ICI 182,780 that abolished the estrogen-induced DNA synthesis (7% of residual BrdU incorporation). The shuffled sequence of peptide SEQ.ID NO.1 (Ss) has not significant effect on estrogen-induced DNA synthesis.

The peptide SEQ.ID NO.1 is finally assayed for its ability to reduce or inhibit EGF induced DNA synthesis in human prostate cancer LNCaP (1C) and MCF-7 (1D) cells. The LNCaP and MCF-7 cells are cultured as described above, then seeded onto coverslips. Cells are then stimulated with 100 ng/ml of highly purified EGF (Boheringer, Calif.) in the absence or in presence of 1 nM peptide SEQ.ID NO.1.

In FIG. 1C, it can be observed that EGF stimulates BrdU incorporation from 8 to 21%. Addition of the peptide reduces to 5,8% BrdU incorporation, similar to the pure antiestrogen, ICI 182,780 (7% of residual incorporation). The shuffled sequence of peptide SEQ.ID NO.1 (Ss) has a little effect on BdrU incorporation (15% of residual incorporation). In MCF-7 cells, as shown in FIG. 1D, EGF also stimulates BrdU incorporation (from 6 to 36%); addition of the peptide reduces to 13% BrdU incorporation, and ICI 182,780 to 9% of residual incorporation. In contrast, the shuffled sequence of peptide SEQ.ID NO.1 (Ss) does not reduce BdrU incorporation (48% of incorporation)

Methods

DNA synthesis is assayed in single cells by a 6 h pulse with 100M (final concentration) BrdU (Boeheringer). Cells on coverslips are fixed, and incubated with diluted (1:1 in PBS) fluorescein-conjugated mouse anti-BrdU mAbs (clone BMC9318 from Boheringer Mannheim Co., Ind.), then washed three times with PBS. Mouse antibodies are revealed using diluted (1:200 in PBS) Texas-red conjugated goat anti-mouse antibodies (Calbiochem, Calif.). All coverslips are washed three times in PBS, inverted and mounted in Moviol (Calbiochem, Calif.) on glass slides. Slides are analyzed using an Axiophot fluorescent microscope (Zeiss).

Example 3: Inhibition of Androgen-Stimulated AR Association with Src by AR-Derived (Src-SH3 Binder) Peptide (SEQ.ID NO. 1

It has been demonstrated that hormone bound AR interacts with SH3 domain of Src kinase probably through a proline stretch (Migliaccio et al., 2000). As a consequence of this interaction, the kinase and the downstream signaling pathways are activated and, finally, DNA synthesis is activated. Use of a small peptide sequences mimicking the domain of AR involved in this interaction should be able to inhibit by competition the AR-Src association and block DNA synthesis. To test this hypothesis LNCaP cells are routinely grown in 5% $CO_2$ in air in RPMI 1640 medium (GIBCO) supplemented with phenol-red, 2 mM L-glutamine (GIBCO), penicillin (100 U/ml), gentamicin (50 µl/ml), insulin (0.2 U.I./ml) and 10% fetal calf serum. The cell are then kept in RPMI 1640 without phenol red and supplemented with glutamine, penicillin, gentamicin and insulin as above and containing 10% charcoal-stripped fetal calf serum for further 4 days. Cells are then stimulated with 10 nM R1881 alone or in the presence of a 1000-fold excess of the anti-androgen Casodex or 1 nM of the SEQ.ID NO.1 peptide or 1 nM of the shuffled sequence of peptide SEQ.ID NO.1 (SEQ.ID NO.7) for 2 min., and lysed. Cell lysates are submitted to immuno-precipitation using mouse monoclonal anti-Src antibodies (Clone 327, Oncogene Science, Manhasset, N.Y.). The immuno-precipitated proteins are resolved on a 12% SDS-polyacrylammide gel and thereafter transferred onto nitrocellulose filters. The filters are incubated with either anti-Src antibodies or mouse monoclonal anti AR antibodies. The immuno-complexes on nitrocellulose filters are revealed using peroxidase-linked anti-mouse antibodies with a chemiluminescent substrate (Pierce Chemicals, Ill.).

As expected, in hormone treated cells, AR is co-immunoprecipitated by anti Src antibodies (FIG. 2A, Lane 2). The association between AR and Src is abolished when LNCaP cells are stimulated with hormone in the presence of Casodex (Lane 3).

Similarly, no AR is co-immunoprecipitated by anti-Src antibodies in cells treated with androgens and SH3 binder peptide. In contrast, the hormone stimulated Src-AR association is only slightly affected by treatment with the same concentration of the shuffled sequence of peptide SEQ ID NO.1(Ss, SEQ.ID NO.7).

Methods

Preparation of cell lysates. Cells are suspended in 1 ml of lysis buffer: 50 mM Tris-HCl, pH 7.40, containing 5 mM MgCl2, 150 mM NaCl, 0,5% Triton X-100 and left under gentle shaking for 2 min, at 4° C. Suspensions are then centrifuged at about 800 g for 30 min and supernatant collected and used for immunoprecipitation.

Example 4: Inhibition of Estrogen-Stimulated ER Association with SRC by AR-Derived (Src-SH3 Binder) Peptide (SEO.ID NO. 1)

It has previously shown that ER together with AR forms a ternary complex with Src (Migliaccio et al., 2000). Inhibition of interaction of either ER or AR with Src leads to disruption of this ternary complex and inhibition of Src-mediated signaling. Therefore inhibition of AR-Src interaction by SH3 binder peptide(s) should also abolish the ERα association with Src and the estradiol induced signal transduction. To address this point mammary cancer derived MCF-7 cells are grown in 5% $CO_2$ in air in DMEM medium (GIBCO) supplemented with phenol-red, 2 mM L-glutamine (GIBCO), penicillin (100 U/ml), gentamicin (50 l/ml), hydrocortisone (3.75 ng/ml) insulin (0.2 U.I./ml) and 5% fetal calf serum. The cells are then kept in DMEM without phenol red and supplemented with glutamine, penicillin, gentamicin and insulin as above and containing 5% charcoal-stripped fetal calf serum for additional 4 days. Cells are then stimulated with 10 nM 17ß estradiol alone or in the presence of a 1000-fold excess of the anti-estrogen ICI 182,780 or 1 nM of the SEQ.ID NO.1 peptide or the shuffled sequence of peptide SEQ.ID NO.1 for 3 min., and lysed. Cell lysates are submitted to immunoprecipitation using mouse monoclonal anti-Src antibodies (Oncogene Science, Manhasset, N.Y.). The immunoprecipitated proteins are resolved on a 12% SDS-polyacrylammide gel and thereafter transferred onto nitrocellulose filters. The filters are incubated with either anti-Src antibodies or mouse monoclonal anti AR antibodies. The immunocomplexes on nitrocellulose filters are revealed using peroxidase-linked anti-mouse antibodies with a chemiluminescent substrate as described above.

As expected, in hormone treated cells ER is co-immunoprecipitated by anti Src antibodies (FIG. 2B, Lane 2). The association between ER and Src is abolished when MCF-7 cells are stimulated with hormone in the presence of ICI 182,780 (Lane 3). No ER is co-immunoprecipitated by anti-Src antibodies in cells treated with androgens and SH3 binder peptide at a concentration of 1 nM. Src-AR association is only slightly affected by treatment with the shuffled sequence of peptide SEQ ID NO.1 at 1 nM (Ss).

Example 5: Inhibition of Androgen-Stimulated Cyclin-d Expression by AR-Y (Src-SH13 Binder) Peptide (SEO.ID NO.1) in Prostate Cancer (LNCAP) and Mammary Cancer (MCF-7) Cells Estrogen and androgen receptors stimulate Src which in turn activates phosphatidyl-3-kinase (PI3-K) pathways (Castoria et al., 2000). Activation of PI3-K leads to PKB/Akt kinase phosphorylation that results in increased Cyclin D expression. This drives hormone dependent cells towards the cell cycle G1/S transition (Castoria et al., 2000). Inhibition of Src or PI3-K causes cell accumulation in G1 phase and block of DNA synthesis. Therefore SH3 binder peptides could be used to inhibit Src kinase and PI-3K dependent Cyclin D1 expression. To verify this possibility, SH3 binder peptide (SEQ.ID NO.1) is added to MCF-7 and LNCaP cells stimulated with the androgen. MCF-7 and LNCaP cells are routinely grown as described above. Cells are then kept for at least 4 days in red phenol-free medium supplemented as described above and added with dextran-coated charcoal treated fetal calf serum to minimize steroid concentration. Cells are then treated with 10 nM R1881 alone or in the presence of 1 nM SH3 binder peptide (SH3, SEQ.ID NO.1) or 1 nM of the shuffled sequence of peptide SEQ.ID NO.1 (SEQ.ID NO.7) (Ss) for 6 hrs, then lysed and submitted to western blot using anti-Cyclin D1 antibodies (FIG. 3A, upper and lower panels). As expected, androgen stimulates Cyclin D1 expression in MCF-7 and LNCaP cells. The PI3-K inhibitor, LY 294,002, at a concentration of 5 μM and the Src inhibitor, PP2 (not shown), abolishes the hormone stimulated cyclin expression. Addition of 1 nM SH3 binder peptide (SEQ.ID NO.1) (SH3) also suppresses Cyclin D induction by R1881 whereas the shuffled sequence of peptide SEQ.ID NO.1 (Ss) only partially reduces this effect.

Example 6: Inhibition of Estrogen-Stimulated Cyclin-d1 Expression by AR-Derived (Src-SH3 Binder) Peptide (SEQ.ID NO. 1) in Prostate (LNCAP) and Mammary (MCF-7) Cancer Cells To test the effect of SH3 binder peptide (SEQ.ID NO.1) on estrogen stimulated Cyclin D1 expression, this peptide is added to LNCaP and MCF-7 cells stimulated with 10 nM 17ß-estradiol (FIG. 3B). MCF-7 and LNCaP cells are routinely grown as reported above. Cells are then kept for at least 4 days in red phenol-free medium supplemented as described above and added with dextran-coated charcoal treated fetal calf serum to minimize steroid contamination. Cells are then treated with 10 nM 17ß estradiol alone or in the presence of either the PI-3K inhibitor LY 294,002 (5 μM) or 1 nM SH3 binder peptide (SEQ.ID NO.1) or 1 nM shuffled sequence of peptide SEQ ID NO.1 (SEQ ID NO.7) for 6 hrs (FIG. 3B, upper and lower panels), then lysed and submitted to western blot using anti-Cyclin DI antibodies as above. Like the androgen, 17l estradiol stimulates Cyclin DI expression. The PI3-K inhibitor, LY 294,002, also in this case abolishes the hormone stimulated cyclin expression. One nM SH3 binder peptide (SEQ.ID NO.1) (SH3) completely suppresses Cyclin D induction by estrogen whereas the shuffled peptide SEQ.ID NO.1 (Ss) has a little effect.

Example 7. Ineffectiveness on Androgen Receptor Dependent Gene Transcription of AR-Derived (Src-sh3 Binder) Peptide (SEQ.ID NO.1) in Prostate Cancer (LNCaP) and Breast Cancer (MCF-7) Cells Steroidal receptors are generally known as ligand activated transcription factors. Therefore, it is important to assess whether SH3-binder anti-androgen peptide effect involves the transcriptional activity of the androgen receptor. LNCaP cells, kept in 5% $CO_2$ in air in RPMI 1640 medium (GIBCO) supplemented with phenol-red, 2 mM L-glutamine (GIBCO), penicillin (100 U/ml), gentamicin (50 µl/ml), insulin and 10% fetal calf serum, are transfected with a reporter gene engineered in a pSG5 expression vector with the luciferase gene under the control of an androgen responsive element (ARE3416) (Verrijdt et al., 2000). Six hrs after transfection, the medium was replaced by fresh medium and cells were left for further 24 hrs in the absence or in presence of 10 nM R1881 alone or with a 1000 fold excess of Casodex or with 1 nM SH3 binder peptide SEQ.ID NO. 1 or 1 nM shuffled peptide SEQ ID NO.1 (SEQ.ID NO.7). Cells lysates are assayed for luciferase activity. The same experiment is repeated to analyze the anti-androgen peptide effect on the transcriptional activity of estrogen receptor in human breast cancer cells. MCF-7 cells, kept in 5% $CO_2$ in air in DMEM medium (GIBCO) supplemented with phenol-red, 2 mM L-glutamine (GIBCO), penicillin (100 U/ml), gentamicin (50 µl/ml), hydrocortisone (3.75 ng/ml), insulin (0.2 U.I./ml) and 5% fetal calf serum, are transfected with a reporter gene QUALE cloned in a pSG5 expression vector with the luciferase gene under the control of an estrogen responsive element. Finally, cells lysates are assayed for luciferase activity.

FIG. 4A shows the luciferase activity in untreated LNCaP cells (bar 1), in cells stimulated with R1881 alone (bar 2) or in presence of either Casodex excess (bar 3), or SH3 peptide (SH3) (bar 4) or shuffled peptide SEQ.ID NO.1(Ss) (bar 5).

FIG. 4B shows the luciferase activity in untreated MCF-7 cells (bar 1), in cells stimulated with 17 β estradiol alone (bar 2) or in presence of either ICI 182,780 excess (bar 3), or the peptide SEQ. ID NO.1 (SH3) (bar 4) or the shuffled sequence of peptide SEQ. ID NO.1 (Ss) (bar 5).

It can be observed that whereas the conventional antiandrogen completely inhibits androgen induced transcription of reporter gene neither the SH3 peptide nor the shuffled sequence of peptide SEQ. ID NO.1 affect transcriptional activity of AR.

Example 8. "In Vivo" Antitumor Effects of the AR Derived. Src-SH3 Binder Peptide (SEQ. ID NO:1

Since results of in vitro and in vivo tumor growth studies can be divergent, it has been studied the growth response of LNCaP and MCF-7 cells to the antiandrogen-peptide in vivo. LNCaP cancer cells, grown under routine conditions above described, are suspended in 50% (vol/vol) Matrigel solution in sterile PBS (pH 7.4) and injected subcutaneously in the dorsal posterior region at $2.5 \times 10^6$ cells/male athymic mice (CD mice, Charles-River) without hormone priming.

After 14-21 days, animals with tumors of similar size are randomized to treatment with SH3 binder-peptide, SEQ.ID NO.1, or vehicle alone for an additional 5 weeks. The treatment is initiated with tumors at approximately 200-400 $mm^3$ in size. Tumor volumes of LNCaP cells xenografts with or without treatments are measured by a caliper and recorded according to the formula $D \times d^2 \times 0.5$, where D is the length and d is the width of tumor.

For peptide treatment of each animal, 200 µl of 20 nM SH3 binder-peptide SEQ. ID NO.1 dissolved in 0.1% DMSO or the same amount of vehicle alone are intraperitoneally administered on alternate days to the mice. Such studies are especially important to assess the efficacy of peptides as potential therapeutic agents in human prostate and breast cancer cells, which express androgen receptor levels commonly found in human malignancies. The dose, the type and the size of these peptides (general formula Si and SEQ. ID NO.1 to SEQ. ID NO.6) and the route of delivery of peptides are all factors that may be determined using ordinary skill in the art.

FIG. 5A shows the growth rate of LNCaP cell xenografts in nude male mice treated with SH3-binder peptide (SH3) or with vehicle alone (ctrl).

The authors observed that in this model, tumor mass were significantly lower in the SH3 treated group when compared to the control group. No difference is found between weight of mice treated with vehicle solution or the peptide (data not shown).

The effect of anti-androgenic peptides is also analyzed on breast cancer MCF-7 cell xenografts established in nude mice (FIG. 5B). In this case MCF-7 cells, previously grown as described above, are suspended in 50% Matrigel (vol/vol) solution in sterile PBS and injected subcutaneously at $2.5 \times 10^6$ cells/animal in athymic male mice. After 14-21 days, animals with similar size tumors are randomized to treatment with SH3 binder-peptide, SEQ.ID. NO.1, or vehicle alone for additional 5 weeks. Tumors at beginning of the treatment measure approximately 1000 $mm^3$. 200 µl/of 20 nM SH3 binder-peptide in 0.1% DMSO or the same volume of vehicle alone are administered on alternate days to the mice intraperitoneally. Tumor volumes of MCF-7 cancer cell xenograft with or without treatment are measured and recorded as reported above. No difference of body weight is found between control mice or peptide treated mice.

Similarly to what was observed for the LNCaP cell xenografts model, the authors also found in the MCF-7 cell xenografts model that tumor mass was lower in the SH3 treated group when compared to the control group. No difference is found between weight of mice treated with vehicle solution or the peptide (data not shown).

At the end of treatment the animals are sacrificed and tumor specimens are assayed for Ki67 antigen and apoptotic cells. Briefly, sections from each specimen are cut at 3-5 micron, mounted on glass and dried overnight at 37° C. All sections are then deparaffinized in xylene, rehydrated through a graded alcohol series and washed in PBS. This buffer is used for all the subsequent washes and for antibody dilution. Light-microscopic examination is performed after staining with hematoxylin/eosin and hematoxylin/Van Gieson. For immunohistochemistry, tissue sections are heated twice in a microwave oven for 5 min each at 700 W in citrate buffer (pH 6) and then processed with the standard streptavidin-biotin-immunoperoxidase method (DAKO Universal Kit, DAKO Corporation, Carpinteria, Calif., USA). Rabbit anti-human Ki67 from DAKO is used at a 1:100 dilution. The primary antibody was incubated for 1 hour at room temperature. Diamino-benzidine is used as the final chromogen, and hematoxylin as the nuclear counterstain. Negative controls for each tissue section are performed leaving out the primary antibody. Positive controls included in each experiment consist of tissue previously shown to express the antigen of interest. Two observers evaluate the staining pattern of the two proteins separately and score the protein expression in each specimen by scanning the entire section and estimating the number of positive cells visible for high-power-field 10×20. The level of concordance, expressed as the percentage of agreement between the observers, is 92%. In the remaining specimens, the score is obtained after collegial revision and agreement. TUNEL reaction is performed using the peroxidase-based Apoptag kit (Oncor, Gaithersburg, Md., USA). TUNEL positive cells are detected with diamino-benzidine and $H_2O_2$ according to the supplier's instructions. Two observers evaluate the staining pattern of the two proteins separately and score the protein expression in each specimen by scanning the entire section and estimating the number of positive nuclei visible for high-power-field 10×20. The level of concordance, expressed as the percentage of agreement between the observers, is 100%.

The authors observed in LNCaP tumor xenograft specimens a significant reduction in the percentage of Ki-67 antigen positive cells (P<0.002, FIG. 6A, left panel) and a significant increase in the number of TUNEL-positive cells (P<0.009, FIG. 6A, right panel) in the SH3 treated group when compared to the control group. A similar result was found for the MCF-7 tumor xenograft specimens (FIG. 6B left and right panel).

Example 9: Preparation of Antibody Compositions

The synthetic peptides and recombinant peptides described above may be used in the generation of an immune response in an animal or an human and for the preparation of antibodies specific for these epitopes. The preparation of vaccines and antibodies is well known to those of skill in the art as described herein above. Briefly, the novel peptides of the present invention may be used as antigens in animals in the following manner:

Each peptide may be coupled to keyhole limpet hemocyanin (KLH) and used to subcutaneously immunize BALB/c mice. Initial injections contain 250 pg protein and the mice are boosted 7 weeks later with 250 μg of the respective KLH-coupled peptide and then bled 1 week later. The polyclonal antibodies produced by the injected mice are tested for their ability to recognize the peptide antigen in an ELISA assay. The Abs are also assayed for their ability to inhibit AR induced DNA synthesis.

REFERENCES

Allen, Choun 1987 FEBS Lett. 223: 42-46
Bodansky M, Bodansky A 1995 The practice of peptide synthesis ($2^{nd}$ edn.), Springer Verlag, Berlin
Boonyaratanakornkit V. et al., 2001 Mol Cell, 8: 269-280
Capecchi C 1980 Cell, 22(2):479-488.
Carpino L A, Han G Y 1972 J. Org. Chem. 37: 3404-3409
Castoria G, Barone M V, Di Domenico M, Bilancio A, Ametrano D, Migliaccio A and Auricchio F 1999 EMBO J. 18: 2500-2510
Chodak G W, et al., 1992 J Urol 147:798-803
Clapp 1993 Clin. Perinatol., 20(1): 155-168
Couvreur, Tulkens, Roland, Trouet, Speiser 1977 FEBS Lett. 84 (2):323-326
Couvreur 1988 Crit. Rev. Ther. Drug Carrier Syst. 5:1-20
Curiel, et al., 1991 Proc. Natl. Acad. Sci. USA, 88 (19): 8850-8854
Dawson N A, Vogelzang N J 2000 Secondary hormonal therapy. In: Resnick M I, Thompson M I, eds. Advanced therapy of prostate disease. Hamilton, Ontario: B C Decker; 378-384
Denis L J, Griffiths K 2000 Sem Surg Oncol 18:52-74
Eglitis, Anderson 1988 6(7): 608-614.
Eglitis, et al., 1988 Avd. Exp. Med. Biol. 241:19-27.
Fields G B, Noble R L 1990 Int. J. Pep Prot Res 35: 161-214
Fowler J E, Whitmore W F 1982 Cancer 49:1373-1377
Fromm, Taylor, Walbot, 1985 Proc. Natl. Acad. Sci. USA, 82(1 7):5824-5828
Gabizon, Papahadjopoulos 1988 Proc. Natl. Acad. Sci. USA 85: 6949-6953
Graham F L and van der Eb A J, 1973 Virology 54(2): 536-539
Hobisch A, et al., 1996 Prostate 28:129-135
Kay B K et al. 2000 FASEB J: 14, 231-235
Lee D 2003 Clin Prostate Cancer 2:13-14
Migliaccio A, et aL, 2000 EMBO J, 19: 5406-5417
Migliaccio A, et al., 1996 EMBO J. 15: 1292-1300
Migliaccio A, et al., 2005 Cancer Res, 65: 10585-10593.
Mohler J L, et al., 1996 Clin Cancer Res 2:889-895
Moinfar F, et al., 2003 Cancer 98: 703-711
Moss G P 1996 Pure and Applied Chemistry 68: 2193-2222
Rink H 1987 Tetrahedron Lett. 28: 3787-3790
Roy A K, et al., 1999 Vit. Horm. 55:309-352
Sadi M V, Walsh P C, Barrack E R 1991 Cancer 67: 3057-3064
Schatzl G, Madersbacher S, Gsur A, Preyer M, Haidinger G, Haitel A, Vutuc C, Micksche M, Marberger M 2002 Prostate 52:130-138
Shi, Liu, Lippman, Dickson, 1994 Human Reprod., 9: 162-173
Siiteri P K, Wilson J D 1974 J Clin. Endocrinol. Metab 38:113-125
Tam J P, Spetzler J C, 1997 Methods Enzymol. 289: 612-37
Tuchscherer G and Mutter M, 1996 Pure&App/. Chem; 68, 11: 2153-2162
van der Kwast T H, Schalken J, Ruizeveld de Winter J A, van Vroonhoven CCJ,
Mulder E, Boersma W, Trapman J 1991 Int J Cancer 48:189-193
Verrijdt et al. 2000 J. Biol. Chem 275: 12298-12305
Wagner E., et al., 1990 Proc. Natl. Acad. Sci. USA, 87: 3410-3414
Williams J C et al. 1998 TIBS: 23, 179-184
Wong and Neumann 1982 Biochim. Biophys. Res. Commun.107(2): 584-587
Yang et al. 1990 Proc. Natl. Acad. Sci. USA, 87: 9568-9572,

The invention claimed is:

1. A synthetic, isolated or purified or partially purified peptide which is effective to inhibit or prevent the interaction of the androgen receptor (AR) with the SH3 domain of the tyrosine kinase Src,
   wherein the synthetic, isolated or purified or partially purified peptide consists of the amino acid sequence of SEQ ID NO: 1.

2. The synthetic, isolated or purified or partially purified peptide according to claim 1 having an anti-tumor activity.

3. The synthetic, isolated or purified or partially purified peptide according to claim 1 further comprising one or more additional proline moieties on the N-terminal portion.

4. The synthetic, isolated or purified or partially purified peptide according to claim 1 for use as a medicament.

5. The synthetic, isolated or purified or partially purified peptide according to claim 1 for use as anti-tumoral agent.

6. The synthetic, isolated or purified or partially purified peptide according to claim 5 for use against cancers expressing androgen receptor alone or together with estradiol receptors.

7. A pharmaceutical composition comprising a pharmaceutically acceptable and effective amount of the synthetic, isolated or purified or partially purified peptide according to claim 1.

8. The composition according to claim 7 wherein said peptide is linked to a carrier molecule and/or is comprised in a lipid composition.

9. The composition according to claim 7 further comprising at least a second anti-cancer agent.

* * * * *

SEQUENCE LISTING

<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: Synthetic Sequence

```
<400> SEQUENCE: 1

Pro Pro Pro His Pro His Ala Arg Ile Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 2

Pro Pro Pro Pro Pro His Pro His Ala Arg Ile Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 3

Pro Pro Pro Pro Pro Pro Pro His Pro His Ala Arg Ile Lys
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 4

Gly Pro Pro Pro Pro Pro Pro Pro Pro His Pro His Ala Arg Ile Lys
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 5

Pro Pro Pro Pro Pro Pro Pro Pro His Pro His Ala Arg Ile
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 6

His Pro His Ala Arg Ile Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Sequence
```

```
<400> SEQUENCE: 7

His Pro Lys Pro Ala Arg Ile Pro His Pro
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 1, 19
<223> OTHER INFORMATION: Xaa is absent or any amino acid or amino acid
      sequence
<220> FEATURE:
<221> NAME/KEY: VARIANT
<222> LOCATION: (3)...(11)
<223> OTHER INFORMATION: Xaa is Pro or absent
<220> FEATURE:
<221> NAME/KEY: VARIANT
<222> LOCATION: (2)...(18)
<223> OTHER INFORMATION: sequence from positions 2-18 may be present in
      1 to 3 copies

<400> SEQUENCE: 8

Xaa Pro Xaa Xaa Xaa Xaa Xaa Xaa Xaa Xaa Xaa His Pro His Ala Arg
1               5                   10                  15

Ile Lys Xaa
```